US 8,527,295 B2

(12) United States Patent
D'Ambrosia

(10) Patent No.: US 8,527,295 B2
(45) Date of Patent: Sep. 3, 2013

(54) SYSTEM AND METHOD FOR AGGREGATING AND PROVIDING SUBSCRIBER MEDICAL INFORMATION TO MEDICAL UNITS

(75) Inventor: Robert Matthew D'Ambrosia, Corona del Mar, CA (US)

(73) Assignee: EMSystems LLC, Milwaukee, WI (US)

( * ) Notice: Subject to any disclaimer, the term of this patent is extended or adjusted under 35 U.S.C. 154(b) by 1237 days.

(21) Appl. No.: 12/061,364

(22) Filed: Apr. 2, 2008

(65) Prior Publication Data

US 2008/0215373 A1 Sep. 4, 2008

Related U.S. Application Data

(63) Continuation of application No. 11/223,653, filed on Sep. 8, 2005.

(51) Int. Cl.
*G06Q 40/00* (2012.01)
(52) U.S. Cl.
USPC .................................................. 705/2; 705/3
(58) Field of Classification Search
USPC ............................................................ 705/2
See application file for complete search history.

(56) References Cited

U.S. PATENT DOCUMENTS

| | | | |
|---|---|---|---|
| 5,530,950 A | | 6/1996 | Medan et al. |
| 5,664,109 A * | | 9/1997 | Johnson et al. ............... 705/2 |
| 6,117,073 A | | 9/2000 | Jones |
| 6,128,002 A | | 10/2000 | Leiper |
| 6,154,726 A | | 11/2000 | Rensimer et al. |
| 6,196,970 B1 | | 3/2001 | Brown |
| 6,250,929 B1 * | | 6/2001 | Kolb et al. .................... 434/238 |
| 6,523,009 B1 | | 2/2003 | Wilkins |
| 6,574,239 B1 * | | 6/2003 | Dowling et al. .............. 370/469 |
| 6,671,350 B1 | | 12/2003 | Oxley |
| 6,728,708 B1 | | 4/2004 | Yotka et al. |
| 6,834,264 B2 | | 12/2004 | Lucas et al. |
| 7,080,083 B2 | | 7/2006 | Kim et al. |
| 7,120,928 B2 * | | 10/2006 | Sheth et al. ...................... 726/4 |
| 7,213,016 B1 * | | 5/2007 | Barmakian ...................... 707/3 |
| 7,328,276 B2 * | | 2/2008 | Alisuag ......................... 709/237 |
| 7,375,647 B2 * | | 5/2008 | Evans et al. ............. 340/825.52 |

(Continued)

OTHER PUBLICATIONS

Final Office Action received for U.S. Appl. No. 12/061,361 dated Feb. 10, 2012 (10 pages).

(Continued)

*Primary Examiner* — Robert Morgan
*Assistant Examiner* — Reginald R Reyes
(74) *Attorney, Agent, or Firm* — Foley & Lardner LLP

(57) ABSTRACT

A system and method for aggregating and providing subscriber medical record information to medical units. The system includes an ICE medical record server that stores a plurality of medical records of respective subscribers. When a subscriber is being attended by a medical unit, the medical unit using a communication device sends an identification number to the server. In response, the server sends the subscriber's medical record to the communication device. The communication device may populate a medical form with the information and display it for use in diagnosing and treating the subscriber. The medical unit may annotate the medical form to document the on-going emergency, and upload it to a professional medical record server, which may provide the information to a medical facility to which the subscriber will be transported. The ICE and/or professional medical record servers may perform statistical analyses of the information in their respective databases for the purpose of performing symptomatic surveillance and other public health analyses.

32 Claims, 16 Drawing Sheets

(56) References Cited

U.S. PATENT DOCUMENTS

| | | | |
|---|---|---|---|
| 7,440,904 B2 * | 10/2008 | Hasan et al. ................ 705/3 |
| 7,441,180 B1 * | 10/2008 | Kaczmarek et al. .......... 715/201 |
| 7,506,022 B2 | 3/2009 | Wang et al. |
| 2001/0044732 A1 | 11/2001 | Maus et al. |
| 2002/0007315 A1 | 1/2002 | Rose |
| 2002/0111830 A1 | 8/2002 | Tahan |
| 2003/0149597 A1 | 8/2003 | Zaleski |
| 2003/0226889 A1 | 12/2003 | Morrison, Jr. |
| 2004/0015372 A1 | 1/2004 | Bergman et al. |
| 2004/0030579 A1 | 2/2004 | Gil et al. |
| 2004/0078217 A1 | 4/2004 | Bacevice et al. |
| 2004/0181461 A1 | 9/2004 | Raiyani et al. |
| 2004/0189718 A1 | 9/2004 | Stein et al. |
| 2004/0267572 A1 | 12/2004 | Emery |
| 2005/0086073 A1 | 4/2005 | Rodes et al. |
| 2005/0131738 A1 | 6/2005 | Morris |
| 2005/0187948 A1 | 8/2005 | Monitzer et al. |
| 2006/0005441 A1 | 1/2006 | Riley et al. |
| 2006/0036619 A1 | 2/2006 | Fuerst et al. |
| 2006/0143052 A1 | 6/2006 | Fotsch et al. |
| 2008/0287749 A1 | 11/2008 | Reuter |

OTHER PUBLICATIONS

Final Office Action received for U.S. Appl. No. 12/061,361 dated Feb. 28, 2011 (23 pages).
Final Office Action received for U.S. Appl. No. 12/061,361 dated Feb. 6, 2013 (31 pages).
Final Office Action received in U.S. Appl. No. 12/061,361 dated Jul. 19, 2010 (20 pages).
Non-Final Office Action received for U.S. Appl. No. 12/061,361 dated Apr. 5, 2010 (25 pages).
Non-Final Office Action received for U.S. Appl. No. 12/061,361 dated Jun. 5, 2012 (9 pages).
Non-Final Office Action received for U.S. Appl. No. 12/061,361 dated Nov. 18, 2010 (27 pages).
Non-Final Office Action received for U.S. Appl. No. 12/061,361 dated Oct. 20, 2011 (10 pages).
Non-Final Office Action received for U.S. Appl. No. 12/061,361 dated Sep. 21, 2012 (15 pages).
Non-Final Office Action received for U.S. Appl. No. 11/223,653 dated May 10, 2010 (24 pages).
Non-Final Office Action received for U.S. Appl. No. 11/734,776 dated Apr. 5, 2010 (24 pages).

* cited by examiner

| FIELD TYPE | FIELD LABEL | DATA FORMAT | DATA |
|---|---|---|---|
| Subscriber's Demographic Information | Last Name | Open Text | Doe |
| | MI | Open Text | M |
| | First Name | Open Text | John |
| | Gender | Drop Down | Male |
| | Date of Birth | Numeric | 1/1/1959 |
| | Age | Numeric | 46 |
| | Height (ft.) | Drop Down | 5 |
| | Height (in.) | Drop Down | 11 |
| | Weight (lbs.) | Numeric | 185 |
| | Home Address 1 | Open Text | 1313 Mockingbird Lane |
| | Home Address 2 | Open Text | N/A |
| | City | Open Text | Irvine |
| | State | Drop Down | CA |
| | Zip | Numeric | 92614 |
| | Home Phone | Numeric | 987-654-3210 |
| | Work Phone | Numeric | 987-654-1230 |
| | eMail Address | Open Text | john.m.doe@domain-name.com |
| | SSN | Numeric | 123-45-6789 |
| Subscriber's In Case of Emergency Information | ICE No. | Random No. | 330298746 |
| | ICE Contact Seq. | Open Text | Jane W. Doe (Wife), Tom Doe (Father)... |
| | ICE Contact Name 1 | Open Text | Jane W. Doe |
| | ICE Home Phone | Numeric | 987-654-3210 |
| | ICE Work Phone | Numeric | 987-654-3245 |
| | ICE Cell Phone | Numeric | 987-654-3387 |
| | ICE eMail | Open Text | jane.w.doe@domain-name.com |
| | ICE Relationship | Open Text | Wife |
| | ICE Comments | Open Text | Use cell phone no. first |
| | ICE Contact Name 2 | Open Text | Tom Doe |
| | * * * | * * * | * * * |
| Subscriber's Medical Insurance and Primary Care Information | Insurance Carrier | Open Text | Global Health Net |
| | Policy No. | Open Text | DFY73GED |
| | Group No. | Open Text | 325476 |
| | Secondary Insurance | Open Text | CureAll Health Group |
| | Policy No. | Open Text | VYR399LTH |
| | Group No. | Open Text | 4573788 |
| | Primary MD | Open Text | Dr. Jacque T. Prescott |
| | Prim. MD Phone | Numeric | 987-673-4725 |
| Subscriber's Health Information | Primary Condition | Drop Down | Diabetes |
| | Blood Type | Drop Down | A+ |
| | Current Med. | Open Text | Glucovance |
| | Dosage | Open Text | 2.5-500 mg |
| | Frequency | Open Text | Twice a day |
| | Allergies | Open Text | Penicillin |
| | Allergic Reactions | Open Text | Latex |
| | Past Medical Hist. | Open Text | History of heart disease |
| | Comments | Open Text | Has limited mobility |

Fig.3

ANNOTATED SUBSCRIBER MEDICAL RECORD

| ICE MEDICAL RECORD | SEE FIGURE 3 | SEE FIGURE 3 |
|---|---|---|
| PATIENT COMPLAINT | Chief Complaint | Shortness of Breath |
| INCIDENT NARRATIVE | Narrative | Arrive to have a 46 meet me at the ambulance stating he thinks he has a chest infestion and feels SOB, pt, PWD, A&Ox 4 in no obvious distress. Pt. states he has been... |
| DISPATCH INFORMATION | Who Created PCR: | Transport 1 |
| | Arrive | 859 |
| | 1st Trans. | Eastern Plumas Health Care |
| | * * * | * * * |
| PHYSICAL ASSESSMENT | Neuro | Checked |
| | Head/Face | Checked |
| | Pulpis LT | Checked |
| | * * * | * * * |
| PROCEDURE ADMINISTERED | First procedure details | Oxygen mask/cannula O2 N/C 2 lpm Attended by Test Goren |
| | Second procedure details | Peripheral IV IV 18 gauge lt. FA TKO Attended by Test Goren |
| PATIENT ASSESSMENT | Time of assessment | 903 |
| | Position | Fowler |
| | Blood Pressure | 116/P |
| | Pulse | 64 |
| | Resp. | 18 |
| | GCS Eye | Spontaneous |
| | Verbal | Oriented |
| | Motor | Obeys commands |
| | Skin Color | Normal |
| | Temperature | Warm |
| | Moisture | Dry |
| | Pain Level | None |
| | ECG | Normal Sinus Rhythm |
| | Remarks | |

Fig.4C

SYSTEM AND METHOD FOR AGGREGATING AND PROVIDING SUBSCRIBER MEDICAL INFORMATION TO MEDICAL UNITS

CROSS-REFERENCE TO RELATED APPLICATIONS

This application claims the benefit of U.S. patent application Ser. No. 11/223,653, entitled "System and Method for Aggregating and Providing Subscriber Medical Information to Medical Units," filed Sep. 8, 2005, which is incorporated by reference.

FIELD OF THE INVENTION

This invention relates generally to information management systems, and in particular, to a system and method for aggregating and providing subscriber medical information to first responding and other medical units.

BACKGROUND OF THE INVENTION

When a person needs emergency medical assistance, a first responding medical unit (typically referred to as a "first responder") is dispatched to assist the person with the emergency. First responding medical units are typically mobile medical units, such as paramedics and emergency medical technicians (EMTs), as well as government emergency medical units such as those under the Federal Emergency Management Agency (FEMA). In an emergency situation, first responding medical units are tasked to provide preliminary diagnosis and treatment in order to stabilize patients for subsequent transportation to hospitals, urgent care centers, or other permanent medical facilities (termed herein as "second responding medical units").

In responding to an emergency, a first responding medical unit typically attempts to obtain as much medical information about the patient in order to assist it in diagnosing and treating the patient. Such medical information typically sought includes the patient's demographic information, in-case-of emergency contact information, health insurance information, primary care information, and patient health information. Generally, a first responding medical unit has a pre-hospital care record (PCR) form or other type of patient medical form in which the first responding medical unit records the patient's medical information. The first responding medical unit typically receives this information directly from the patient.

However, in many emergency medical situations, a patient is unconscious and unable to provide such medical information to the first responding medical unit. And, even if such patient is conscious, the patient may not be able to provide accurate information because of his/her emotional and medical state. In addition, if the patient is able to provide accurate information to the first responding medical unit, the medical unit has to manually enter all that information into a PCR form. Further, when the patient is subsequently transported to a second responding medical unit, a new PCR for the patient may need to be created.

SUMMARY OF THE INVENTION

An aspect of the invention relates to a communication system that provides medical record information of a subscriber to a medical unit in order to assist the medical unit with diagnosis and treatment of the subscriber during an on-going medical emergency. The communication system also assists the medical unit with the completion of an electronic patient medical record form (e.g., a pre-hospital care record (PCR) form), and with the subsequent transmission of the electronic patient medical record to a medical unit to which the subscriber will be transported. In particular, the communication system comprises an ICE medical record server and a network. The ICE medical record server contains a plurality of data objects pertaining to medical records of subscribers. The ICE medical record server is adapted to receive an ICE identification number associated with a data object from a communication device operated by a medical unit by way of the network. In response to receiving the ICE identification number, the medical record server accesses the medical record data object associated with the ICE identification number, and sends the medical information in the data object to the communication device of the medical unit by way of the network.

The ICE medical record server is also adapted to enroll subscribers who desire their respective medical information to be sent to medical units in the case of medical emergencies. In this regard, the ICE medical record server initially receives an enrollment request from a candidate subscriber communication device via the network. The enrollment request contains the subscriber's medical record information. In response to receiving the request, the ICE medical record server creates a data object for the candidate subscriber's medical record, and generates an ICE identification number associated with the data object. The ICE medical record server then generates and sends the medical information along with the ICE identification number to the subscriber with instructions to keep the identification number on hand by any of a number of means.

The ICE medical record server is also adapted to allow subscribers to edit their respective medical records to ensure that the information is current and accurate, and also allow the subscribers full control of the information residing in their respective medical records. In this regard, the medical record server receives a request to edit medical information in the subscriber's medical record data object. The request is received from a subscriber's communication device by way of the network. In response to the request, the ICE medical record server determines whether the request comes from the subscriber (i.e., an authorized party). If the ICE medical record server determines that the request is valid, the ICE medical record server allows the subscriber to send the edits to the information in his/her medical record data object. After the subscriber enters and submits the desired edits, the ICE medical record server receives the edits from the subscriber's communication device via the network, and updates the corresponding data object.

The ICE medical record server may also be adapted to perform statistical analysis on the subscribers' medical record information upon request from an authorized third party. For example, the statistical analysis may be requested by a government agency or medical institution monitoring the general health of subscribers and conducting symptomatic surveillance for certain medical conditions. In this regard, the ICE medical record server receives a request for statistical information based on input parameters. The ICE medical record server then performs the requested statistical analysis, generates a report containing the results of the statistical analysis, and sends it to the communication device via the network. The request received by the ICE medical record server may also be for providing on-going statistical information and/or alerts to the requesting party, so that the requesting party can continuously monitor the current health of the defined public and receive alerts when certain health problems exceed normal levels.

Another aspect of the invention relates to a communication device used by a medical unit that is adapted to obtain medical information about a subscriber who is in need of emergency medical assistance. The communication device is adapted to send an ICE identification number to the ICE medical record server. Subsequently, the communication device receives the medical information in the subscriber medical record data object corresponding to the ICE identification number. The communication device may be able to pre-populate an electronic patient medical record form (e.g., a PCR form) with the information. The communication device also causes the electronic patient medical record to be displayed on a output device to allow the medical personnel to view the information. In this way, the medical information may assist the medical personnel in diagnosing and treating the subscriber.

The communication device further allows the medical personnel to annotate the electronic patient medical record with information concerning the on-going emergency. In addition, the communication device also allows the medical personnel to send the annotated electronic patient medical record to a professional medical record server, which stores annotated medical records (e.g., PCRs) of many subscribers. The communication device may further be adapted to send a request to the professional medical record server to send the annotated subscriber medical record to a medical facility to which the subscriber is to be transported. In this way, the medical facility that is to receive the subscriber has pre-knowledge of the subscriber's medical history and on-going medical condition, and can prepare for diagnosis and treatment before the subscriber arrives.

Another aspect of the invention relates to a professional medical record server, which, as discussed above, stores annotated medical records (e.g., PCRs) of many subscribers, and provides the annotated medical records to authorized parties upon request. The professional medical record server may also perform the same statistical analysis and reporting as performed by the ICE medical record server.

Other aspects, features, and techniques of the invention will be apparent to one skilled in the relevant art in view of the following detailed description of the invention.

BRIEF DESCRIPTION OF THE DRAWINGS

FIG. 3 illustrates a diagram of an exemplary subscriber medical record in accordance with another embodiment of the invention;

FIG. 4C illustrates a diagram of an exemplary annotated patient medical record (e.g., a PCR) in accordance with another embodiment of the invention;

DETAILED DESCRIPTION OF THE EXEMPLARY EMBODIMENTS

Figure 1:
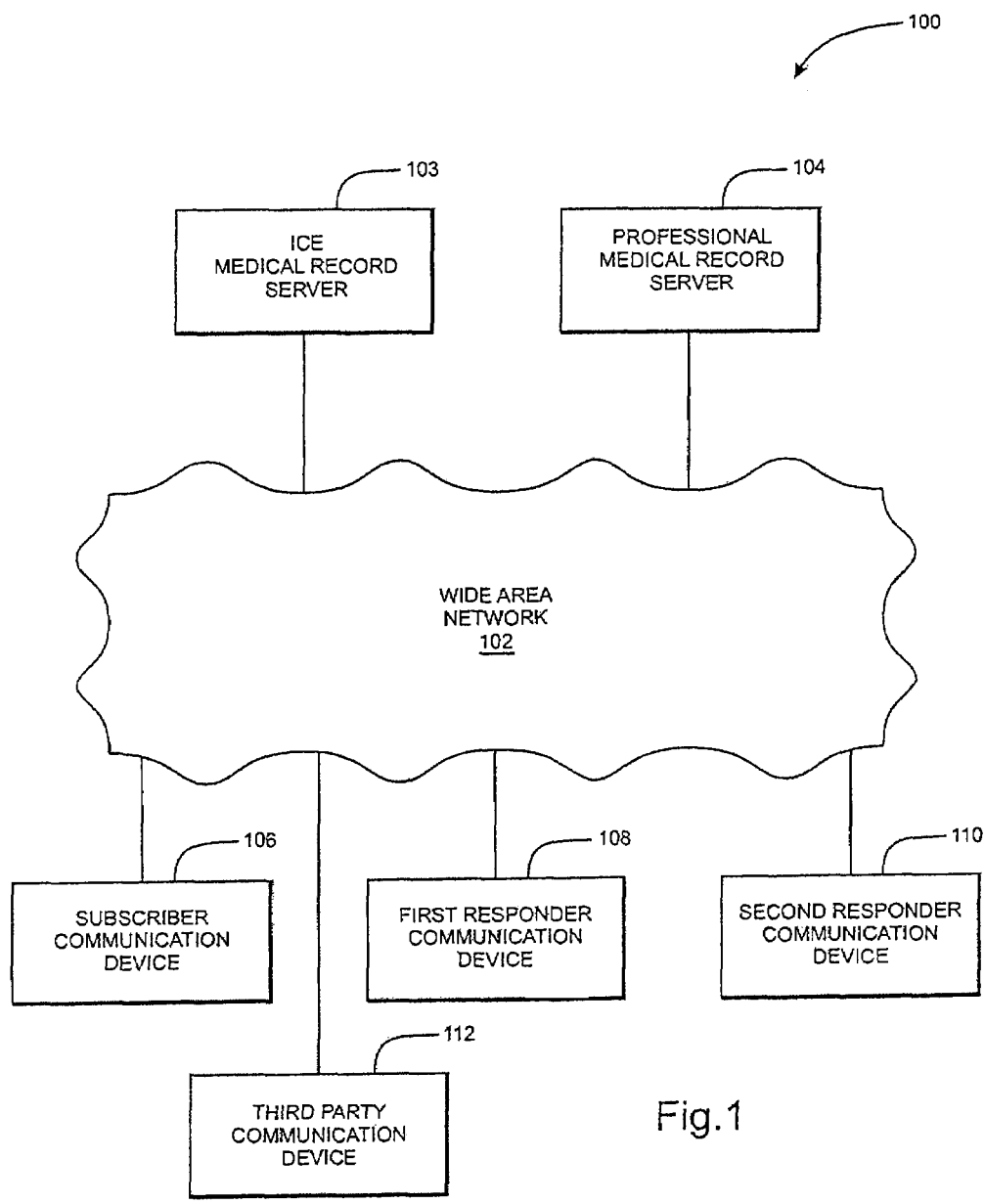
FIG. 1 illustrates a block diagram of an exemplary communication system in accordance with an embodiment of the invention.

FIG. 1 illustrates a block diagram of an exemplary communication system 100 in accordance with an embodiment of the invention. In summary, the communication system 100 provides subscriber medical information to medical units providing diagnosis and treatment to subscribers in emergency situations. The communication system 100 includes an in-case-of-emergency (ICE) medical record server that stores a plurality of medical records (i.e., data objects) containing medical information pertaining to subscribers. Upon receiving an in-case-of-emergency (ICE) identification number associated with a medical record data object of a particular subscriber, the ICE medical record server sends the corresponding medical information to the requesting medical unit.

During the enrolling of a subscriber, the ICE medical record server receives medical information from the subscriber. Using the medical information received, the ICE medical record server creates a medical record data object containing the medical information of the subscriber. Also, during the enrollment process, the ICE medical record server generates and sends an ICE identification number associated with the subscriber's medical record data object to the enrolling subscriber. The subscriber generally keeps the ICE identification number on him/her at all times.

When the subscriber is in a medical emergency situation, a first responding medical unit (e.g., a paramedic, emergency medical technician (EMT), or FEMA agent) obtains the ICE number from the subscriber. Using a communication device, the first responding medical unit sends the ICE number to the ICE medical record server. In response, the ICE medical record server accesses the subscriber's medical record data object using the ICE number, and sends the corresponding medical information to the communication device of the first responding medical unit. Having the medical record information of the subscriber on hand, the first responding medical unit may be able to better diagnose and treat the subscriber. The communication device of the first responding medical unit may also be able to pre-populate an electronic patient medical record form (e.g., a pre-hospital care record (PCR) form) with the medical information received from the ICE medical record server. The first responding medical unit using its communication device may annotate the patient medical record form to document the on-going emergency.

The communication system 100 also includes a professional medical record server adapted to receive annotated medical record forms (e.g., a pre-hospital care record (PCR) form) from first responding medical units, store the annotated medical record forms, and provide the annotated medical record forms to other authorized medical units and government agencies upon request. That is, after a first responding medical unit has pre-populated an electronic patient medical record form with the information it has received from the ICE medical record server, the first responding medical unit using its communication device sends the annotated patient medical record to the professional medical record server. The professional record server then creates a data object containing the information from the annotated medical record form of the subscriber.

If the first responding medical unit determines that the subscriber needs to be taken to a second responding medical unit (e.g., hospital, urgent care facility, medical clinic, etc.), the first responding medical unit may send a request to the professional medical record server to send the annotated medical information of the subscriber to a communication device used by the second responding medical unit. In response to the request, the professional medical record server sends the information to the communication device operated by the second responding medical unit. Alternatively, the second responding medical unit using its communication device may itself request the information from the professional medical record server. Having the annotated medical record information of the subscriber on hand, the second responding medical unit may be able to better diagnose and treat the subscriber.

Both the ICE and professional medical record servers may further be adapted to perform statistical analysis on their respective subscriber medical record databases on behalf of authorized third parties. In this regard, any of the medical record servers receives a request for a statistical analysis report from the communication device of an authorized third party. In the request, the input parameters for the requested statistical analysis may be provided. In response to the request, any of the medical record servers performs the requested statistical analysis based on the input parameters, generates a report containing the results of the statistical analysis, and sends the report to the communication device of the authorized third party. In addition, any of the medical record servers may be configured to receive a request to monitor for certain specified medical conditions on an on-going basis, and send statistical information related to the specified medical conditions to the communication device of the requesting party on an on-going basis. Further, any of the medical record servers may be adapted to send alerts to the communication device of the requesting party when the number of occurrences of specified medical conditions exceed a threshold. This allows a medical institution and/or government agency to perform symptomatic surveillances for outbreaks of certain types of illness and diseases. The communication system 100 will now be described with reference to a more concrete example.

The communication system 100 comprises an ICE medical record server 103, a professional medical record server 104, a subscriber communication device 106, a first responding medical unit communication device 108, a second responding medical unit communication device 110, and a third party communication device 112, all of which are coupled to each other by way of a wide area network 102. The ICE and professional medical record servers 103 and 104 and the communication devices 106, 108, 110 and 112 may be coupled to the wide area network 102 (e.g., the Internet) each by way of a wired and/or wireless communication link. Although the ICE and professional medical record servers 103 and 104 are shown as separate servers, it shall be understood that the respective operations of these servers 103 and 104 may be implemented on a common server. The communication devices 106, 108, 110, and 112 may be any device capable of sending and receiving data to and from the ICE and/or professional medical record servers 103 and 104 by way of the wide area network 102. Such devices include desktop computers, laptop computers, cellular telephones, personal digital assistants (PDA), mobile data terminals, etc.

The following describes various methods implemented by the exemplary communication system 100 including an exemplary method of enrolling a candidate subscriber for the emergency medical assistance provided by the ICE medical record server; an exemplary method of providing the subscriber's medical record information to a first responding medical unit; an exemplary method of providing a subscriber medical record information to a second responding medical unit; an exemplary method of providing a statistical information related to the subscribers' medical record information stored in the ICE or professional medical record server to a requesting third party; and an exemplary method of monitoring for certain medical conditions performed by the ICE or professional medical record server.

Figure 2:
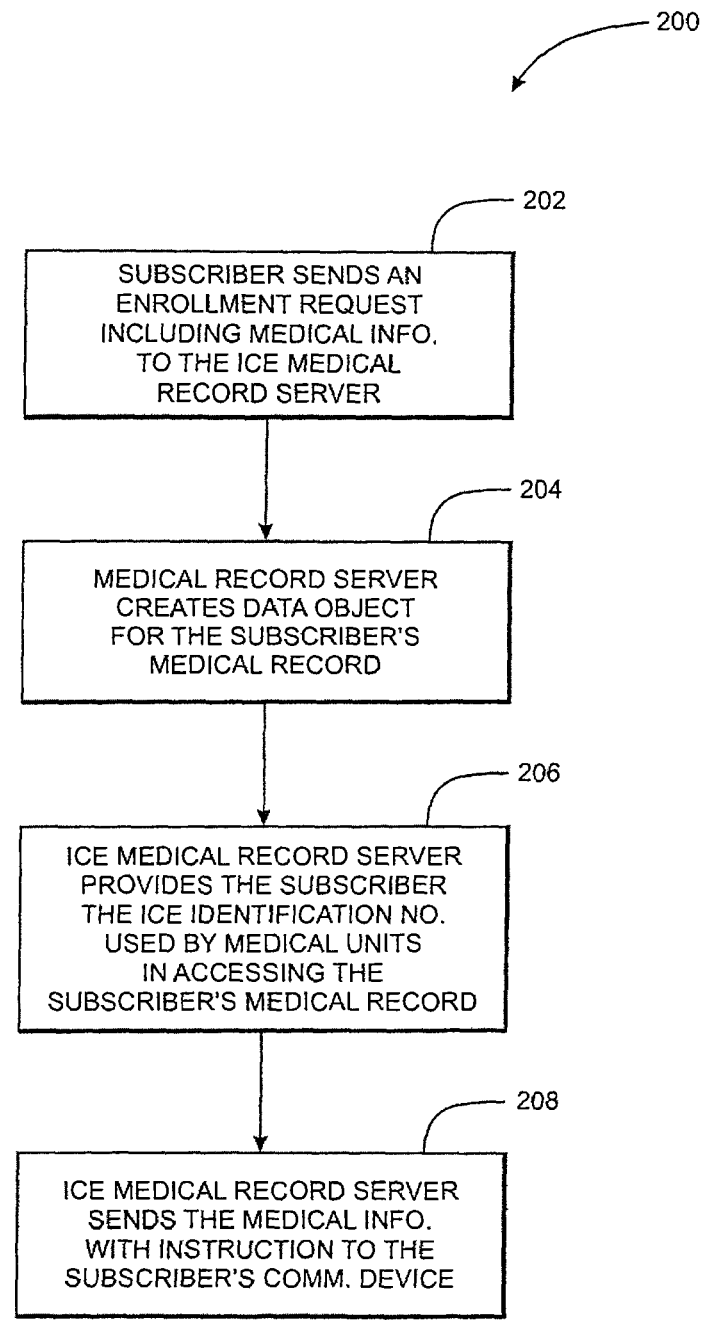
FIG. 2 illustrates a flow diagram of an exemplary method of enrolling a candidate subscriber for emergency medical assistance in accordance with another embodiment of the invention.

FIG. 2 illustrates a flow diagram of an exemplary method 200 of enrolling a candidate subscriber for emergency medical assistance in accordance with another embodiment of the invention. It shall be understood that the candidate subscriber may or may not pay money to receive such service. According to the method 200, a candidate subscriber using the subscriber communication device 106 sends an enrollment request containing his/her medical information to the ICE medical record server 103 by way of the wide area network 102 (block 202). The sending of the enrollment request may be performed in many different manners. For example, upon request the ICE medical record server 103 may send a webpage (e.g., a hyper text markup language (HTML) file) including an input data object for receiving medical record information from the candidate subscriber. As discussed in more detail below, such medical record information may include the subscriber's demographic information, in-case-of-emergency contact information, medical insurance and primary care information, and his/her health information. The input data object may also be adapted to receive login information (e.g., a username and password) from the candidate subscriber to be used by the subscriber in obtaining access to his/her medical record for editing purposes, as discussed in more detail below. After the subscriber enters and submits the requested enrollment medical information, the information is sent to the ICE medical record server 103 by way of the wide area network 102.

After receiving the enrollment request including the candidate subscriber's medical information, the ICE medical record server 103 creates a medical record data object for organizing and accessing the subscriber's medical information, and stores the data object in a local memory (block 204). Once the ICE medical record server 103 has created the medical record data object for the subscriber, the ICE medical record server 103 generates and sends an ICE identification number associated with the data object to the subscriber communication device 106 by way of the wide area network 102 (block 206). As discussed in more detail below, the ICE identification number is used by a first responding medical unit to access the subscriber's medical record information when providing medical diagnosis and treatment to the subscriber in an emergency situation. The ICE medical record server 103 may provide the identification number to the subscriber communication device 106 in a number of ways, such as by generating and sending an email containing the identification number, by generating and sending a webpage containing the identification number, and/or by other manners.

The ICE medical record server 103 then sends the subscriber's medical record information to the subscriber's communication device with instructions on what to do with the information and the ICE identification number (block 208). This may be done in many different ways. For example, the ICE medical record server 103 may dynamically generate and send a webpage (e.g., an HTML file) containing the subscriber's medical record information to the subscriber communication device 106 by way of the wide area network 102. The ICE medical record server 103 may configure the webpage such that some or all of the medical information including the ICE identification number is printable on a wallet-size space. The webpage may further contain instructions for the subscriber to print the webpage, cut out the wallet-size space containing the medical information, laminate the cut-out, and place the laminated cut-out into his/her wallet. The webpage may, additionally, provide instructions to the subscriber to enter the ICE identification number along with a website address associated with a webpage for accessing the subscribers' medical record into the subscriber communication device 106 and/or onto a bracelet or a radio frequency identification (RFID) tag to be worn by the subscriber. This could also assist a first responding medical unit to easily obtain the ICE identification number, and subsequently obtain the subscriber's medical record information using the ICE identification number.

FIG. 3 illustrates a diagram of an exemplary subscriber medical record in accordance with another embodiment of the invention. As discussed above, the exemplary subscriber medical record includes information that is typically requested by a pre-hospital care record (PCR) form. This would facilitate the seamless transfer of the information from the ICE medical record server to a medical unit. In particular, the subscriber medical record may be organized into several field types, for example, subscriber's demographic information, subscriber's in-case-of emergency contact information, subscriber's medical insurance and primary care information, and subscriber's health information.

For each field type, there may be several fields containing certain information about the subscriber. For instance, within the subscriber's demographic information field type, the fields may include subscriber's last name, middle initial (MI), first name, gender, date of birth, age, height, weight, home address, home and work telephone numbers, email address, and social security number (SSN). Each of the fields includes a data format. For example, the last name, middle initial (MI), first name, and home address may have an open text data format allowing a subscriber to enter text into the corresponding fields. The gender, height, and state may have a drop down data format. Whereas, the date of birth, age, weight, zip code, telephone numbers, and SSN may have a numeric data format. An example subscriber's demographic information field for subscriber, John M. Doe, is shown.

Within the subscriber's in-case-of-emergency contact information field type, the fields may include the data object identification number, contact sequence, contact name, contact telephone numbers, contact email address, relationship to the subscriber, and comments. The identification number includes a read-only random number data format. The contact sequence, name, email, relationship and comments may have an open text data format. And, the contact telephone numbers may have a numeric data format. As this example illustrates, subscriber, John M. Doe, has listed Jane W. Doe, his wife, as the primary in-case-of-emergency contact, and Tom Doe, his father, as the secondary in-case-of-emergency contact.

Within the subscriber's medical insurance and primary care information field type, the fields include insurance carrier, policy number, group number, secondary insurance, policy number for the secondary insurance, group number for the secondary insurance, the primary physician, and the primary physician's telephone number. All of the fields in this field type may have an open text data format, except for the primary's physician telephone number, which may be of the numeric type. As this example illustrates, subscriber, John M. Doe, has Global Health Net as his primary insurance, CureAll Health Group as his secondary insurance, and Dr. Jacque T. Prescott as his primary care physician.

Within the subscriber's health information field type, the fields may include primary condition, blood type, current medication, dosage, frequency, allergies, allergic reactions, past medical histories, and comments. All of the fields of this field type may have an open text data format. In this example, the subscriber, John M. Doe, has diabetes as his primary condition, has A+ as his blood type, takes 2.5-500 mg of Glucovance twice a day, is allergic to penicillin, has allergic reactions to latex, has a past history of heart disease, and also has limited mobility. It shall be understood that the medical record is merely an example, and the amount and nature of the information it contains may vary.

Figure 4A:
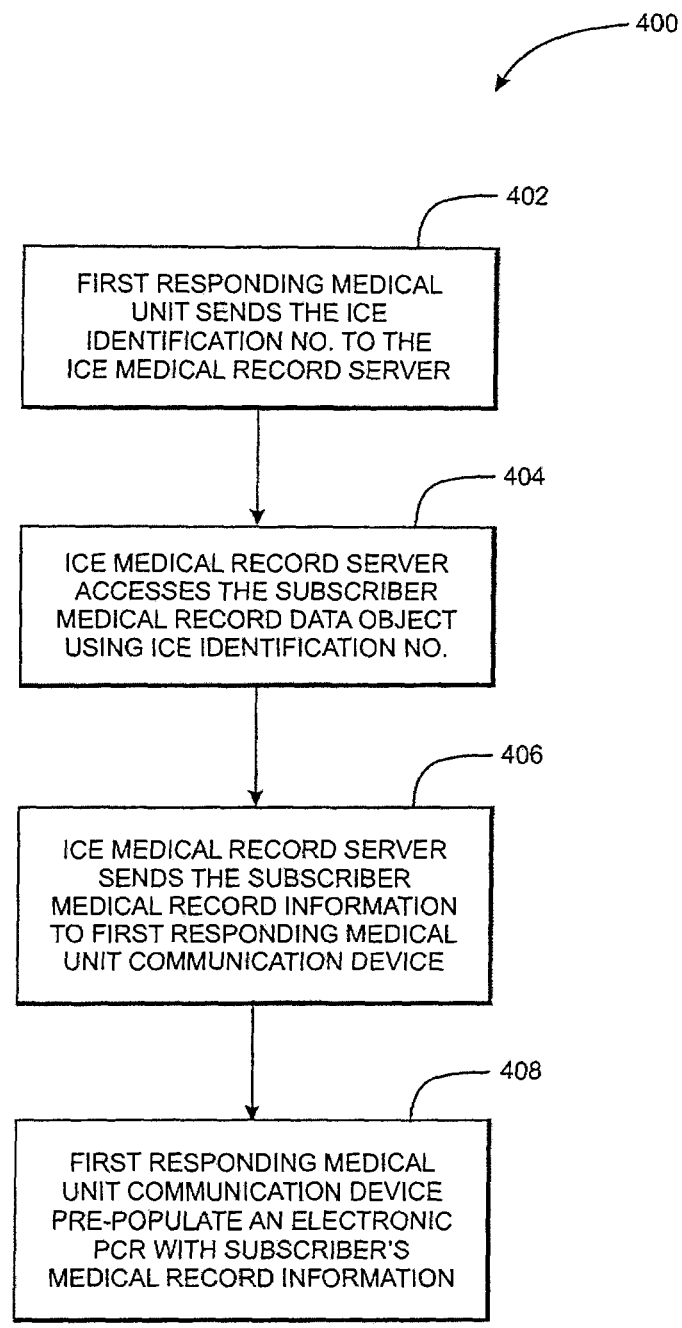
FIG. 4A illustrates a flow diagram of an exemplary method of providing subscriber medical record information to a first responding medical unit in accordance with another embodiment of the invention.

FIG. 4A illustrates a flow diagram of an exemplary method 400 of providing subscriber medical record information to a first responding medical unit in accordance with another embodiment of the invention. The method 400 arises when a subscriber is in a medical emergency situation and the first responding medical unit is attempting to diagnose and treat the subscriber. According to the method 400, the first responding medical unit using its communication device 108 sends the ICE identification number to the ICE medical record server 103 by way of the wide area network 102 (block 402). This may be accomplished in many different ways, such as by performing a digital transfer. Or, as another example, the first responding medical unit using its communication device 108 may access a data retrieval webpage (e.g., an HTML file) generated by the ICE medical record server 103 by way of the wide area network 102. The data retrieval webpage may have an input data object for receiving the ICE identification number associated with the medical record data object of the subscriber. Using the input data object, the first responding medical unit enters and submits the ICE identification number to the ICE medical record server 103. As previously discussed, the subscriber may have the ICE identification number in a laminated card located in his/her wallet, stored in the subscriber communication device, and/or recorded onto a bracelet or RFID tag. The first responding medical unit may search the subscriber for these items to obtain the ICE identification number.

In response to receiving the ICE identification number, the ICE medical record server 103 accesses the subscriber's medical record data object using the ICE identification number (block 404). Then, the ICE medical record server 103 sends the corresponding medical information to the communication device 108 of the first responding medical unit by way of the wide area network 102 (block 406). The communication device 108 of the first responding medical unit may pre-populate an electronic patient medical record form (e.g., a pre-hospital care record (PCR) form) with the received information from the ICE medical record server 103 (block 408). Obtaining the subscriber's medical information while addressing the subscriber's emergency medical condition may assist the first responding medical unit in properly diagnosing and treating the medical conditions. In addition, the pre-populating of the subscriber's medical information into an electronic patient medical record form eliminates the need to populate the form manually.

Figure 4B:
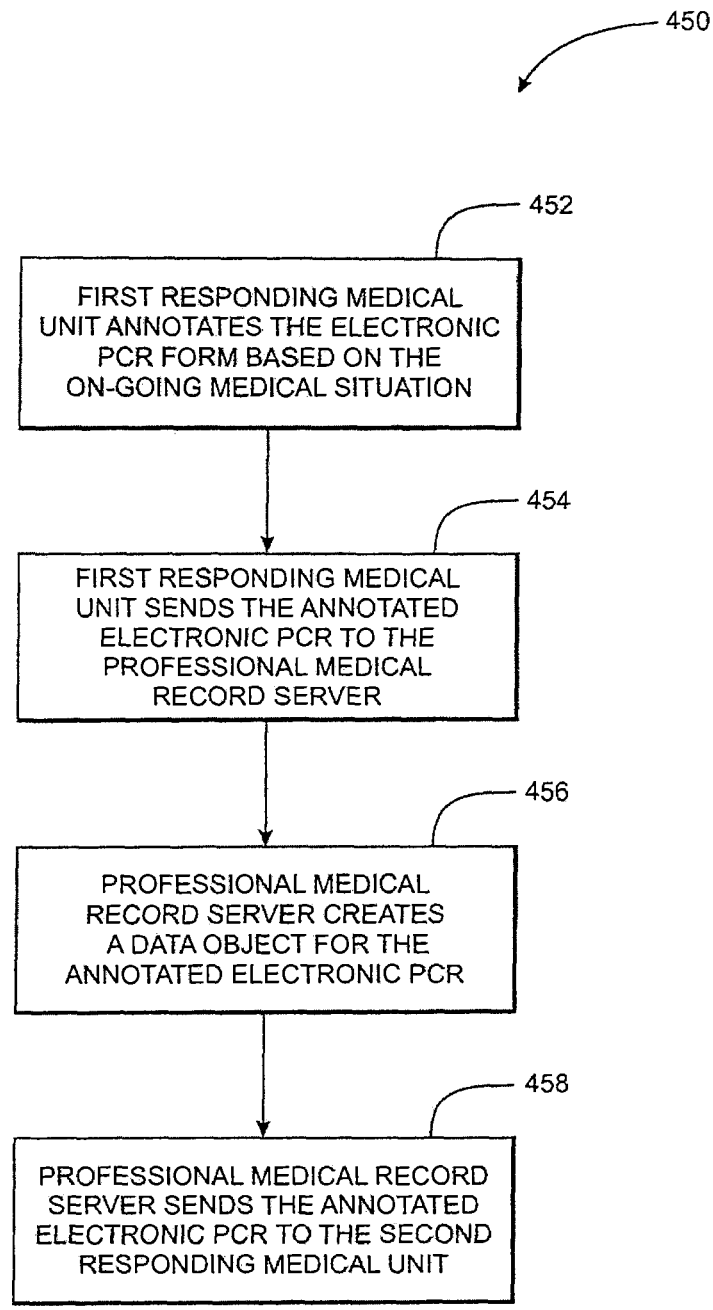
FIG. 4B illustrates a flow diagram of an exemplary method of providing a subscriber medical record information to a second responding medical unit in accordance with another embodiment of the invention.

FIG. 4B illustrates a flow diagram of an exemplary method 450 of providing an annotated subscriber medical record information to a second responding medical unit in accordance with another embodiment of the invention. The method 450 arises after the communication device of the first responding medical unit has received the subscriber's medical information from the ICE medical record server and pre-populated an electronic patient medical record form with the information. According to the method 450, the first responding medical unit using its communication device 108 annotates the electronic patient medical record based upon the on-going medical emergency situation (block 452). For example, the first responding medical unit may annotate the electronic patient medical record with the subscriber's primary symptom(s) (e.g., dizziness, shortness of breath, nausea, etc.) and the subscriber's vital signs. In addition, the first responding medical unit may verify the information that was present in the subscriber's medical record, and annotate the medical record to correct any discrepancies. An exemplary annotated electronic PCR is shown in FIG. 4C, discussed in more detail below.

After annotating the electronic patient medical record form, the first responding medical unit using its communication device 108 sends the electronic patient medical record form to the professional medical record server 104 by way of the wide area network 102 (block 454). The professional medical record server 104 then creates a data object for the annotated electronic patient medical record, and stores it in a local memory (block 456). As previously discussed, although the ICE medical record server 103 and professional medical record server 104 are shown as separate servers for illustrative purposes, it shall be understood that both their functionality may reside on a common server. The professional medical record server 104 may then send the annotated patient medical record to the communication device 110 of the second responding medical unit 110 via the wide area network 102 (block 458). The professional medical record server 104 may send the annotated medical record to the communication device 110 of the second responding medical unit upon request from the first responding and/or second responding medical unit(s).

As discussed above, the second responding medical unit may be, for example, a hospital, urgent care facility, medical clinic, or other medical facility to which the first responding medical unit will transport the subscriber for further medical diagnosis and treatment. For example, if the first responding medical unit determines that the subscriber may be in need of an emergency surgery, the second responding medical unit may use the annotated electronic patient medical record to prepare the surgery room for the incoming patient. It shall be understood that the professional medical record server 104 may send the annotated patient medical record to the second responding medical unit in many ways, such as by email, facsimile, modem, and/or by other manners. Additionally, the professional medical record server may send the annotated patient medical record to a government agency or other entity upon an authorized request.

FIG. 4C illustrates a diagram of an exemplary annotated subscriber medical record (e.g., a PCR) in accordance with another embodiment of the invention. The annotated subscriber medical record includes the subscriber medical information received from the ICE medical record server, and information in which a first responding medical unit has added based on the on-going medical emergency. Such annotations include the subscriber's chief complaint (e.g., shortness of breath, . . . ), a narrative of the incident emergency (e.g., "arrive to have a 46 meet me, . . . ), information related to the first responding medical unit dispatched to assist the subscriber (e.g., Who Created PCR—Transport 1, time of arrival—0859, 1st Trans—Eastern Plumas Health Care, . . . ), information related to the physical assessment of the subscriber (e.g., Neuro—Checked, Head/Face—Checked, Pupils LT—Checked, . . . ), information related to procedure administered (first procedure—Oxygen mask/cannula . . . , second procedure—Peripheral IV, IV 18 gauge lt . . . , . . . ), and information related to the patient's assessment (e.g., Time of assessment—0903, position—Fowler, Blood pressure—116/P, . . . ). Again, this is merely exemplary, and the nature and degree of the information in the annotated subscriber medical record may vary substantially.

Figure 5A:
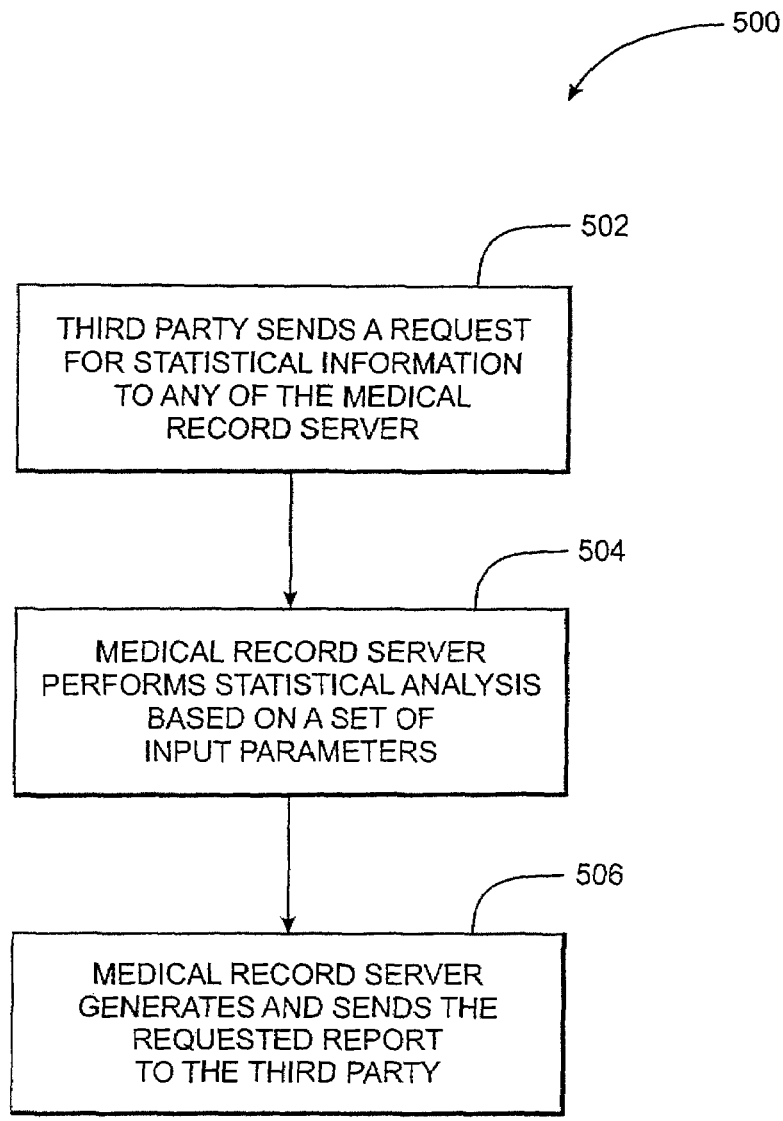
FIG. 5A illustrates a flow diagram of an exemplary method of generating and providing statistical information related to the subscribers' medical record information in accordance with another embodiment of the invention.

FIG. 5A illustrates a flow diagram of an exemplary method 500 of generating and providing statistical information related to the subscribers' medical record information in accordance with another embodiment of the invention. Since both the ICE medical record server 103 and the professional medical record server 104 hold medical information pertaining to many subscribers, they can provide valuable statistical information related to the public health as a whole or within a predefined geographical region. Because the ICE medical record server 103 contains information related to the subscribers' medical histories, and the professional record server 104 additionally contains information related to diagnosis and treatment of subscribers' performed by first responding medical units, each of the medical record server 103 and 104 can provide unique set of statistical information.

As an example, a medical institution may have noticed a higher occurrence of a certain disease contracted by patients recently seen by the medical institution. The medical institution may want to determine whether the higher occurrence of this disease is by happenstance or whether there is a particular cause for the recent outbreak. The medical institution may send a request to any of the medical record servers 103 and 104 to perform a historical statistical analysis regarding patients living in a defined geographical area that have contracted the disease over the last year. The request may be for an immediate feedback whereby the server performs the requested analysis and then sends the analysis report to the requesting party. Alternatively, the request may be for the server to monitor over time for the occurrence of specific symptoms, illnesses, and/or diseases, and provide on-going statistical information regarding the occurrence of such symptoms, illnesses, and/or diseases; and/or send an alert message to the requesting party if the occurrence of such specific symptoms, illnesses, and/or diseases exceed a predetermined threshold. This is an example of symptomatic surveillance whereby medical institutions and/or government agencies monitor for the outbreaks of illnesses and diseases; and thereby, have an assessment of the health of the public as a whole or within a pre-defined geographical area.

In case of a wide area disaster, the statistical information provided by any of the medical record servers 103 and 104 may be extremely valuable to a government agency and/or medical institution in assessing the affected public's medical state and needs. For example, a government agency dealing with a wide area disaster may want a landscape analysis of the victims and the nature of their injuries in order to better develop a plan to provide sufficient and proper resources to effectively and efficiently assists the victims. The government agency may be able to obtain this information by sending a request to the professional medical record server 104, which contains information related to the recent treatment of victims performed by first responding medical units. The professional medical record server 104 is able, in a relatively short time frame, provide the statistical information to the requesting party. Again, such information would be extremely valuable to a government agency, such as FEMA. This example and the prior example are merely illustrative. The nature of the requested statistical report may vary substantially depending on the information being sought. The following describes a couple of exemplary methods of requesting and receiving statistical information from any of the medical record servers 103 and 104.

According to the first method 500 as illustrated in FIG. 5A, a third party using the communication device 112 sends a request for statistical information related to subscriber medical record information to any of the medical record server 103 and 104 by way of the wide area network 102 (block 502). This can be accomplished in many ways, such as by the requesting party accessing a report request webpage (e.g., an HTML file) provided by the target medical record server via the wide area network 102. It shall be understood that the third party may need to submit login information to obtain access to the report request webpage. In this way, only authorized entities are allowed to request statistical analysis reports from the target medical record server. The report request webpage may include an input data object to receive the input parameters for the statistical analysis. Such input parameters may include delimiters such as gender, age, geographical area, primary condition, blood type, chief complaint, patient assessment, procedure administered, etc., as well as the requested outputs such as the number of subscribers and percentage of subscribers meeting the criteria, etc. Accordingly, after receiving the report request webpage, the third party using the communication device 112 enters and sends the input parameters for the requested report to the target medical record server via the wide area network 102.

The target medical record server then receives the input parameters for the requested report, and based on those parameters, performs the requested statistical analysis (block 504). After performing the statistical analysis, the target medical record server generates and sends the requested report to the communication device 112 operated by the requesting third party via the wide area network 102 (block 506). This may be performed by the target medical record server by dynamically generating a webpage containing the report summary, and sending the webpage to the third party communication device 112 via the network 102. This is an example of sending a request for the purpose of receiving an immediate response. The following example relates to sending a request for on-going statistical analysis and reporting.

Figure 5B:
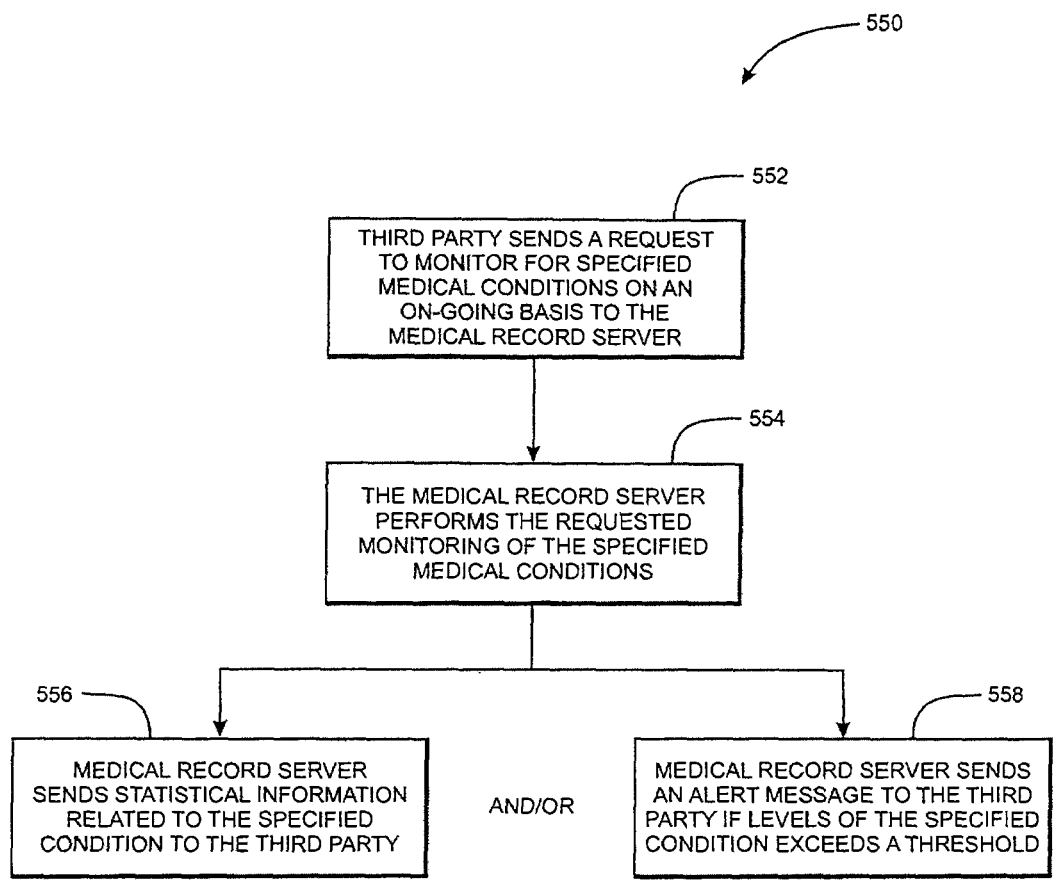
FIG. 5B illustrates a flow diagram of another exemplary method of generating and providing on-going statistical information related to the subscribers' medical record information in accordance with another embodiment of the invention.

FIG. 5B illustrates a flow diagram of another exemplary method 550 of generating and providing statistical information related to the subscribers' medical record information in accordance with another embodiment of the invention. According to the method 550, an authorized third party using the communication device 112 sends a request to monitor for certain medical conditions (e.g., symptoms, illnesses, diseases, etc.) on an on-going basis to any of the medical record servers 103 and 104 by way of the wide area network 102 (block 552). After receiving the request, the target medical record server performs the requested monitoring of the specified condition on an on-going basis (block 554). The target medical record server may, if requested, send statistical information related to the specified condition to the communication device 112 of the requesting third party by way of the wide area network 102 (block 556). In this way, the third party, for example, a government agency, can monitor the levels of certain symptoms, illnesses, and/or diseases on an on-going basis. Alternatively, or in addition to, the target medical record server may send an alert message to the communication device 112 of the requesting third party by way of the wide area network 102, if and when the levels of the specified medical condition exceed a predetermined threshold (block 558). In this way, the third party, for example, a government agency, is quickly alerted to outbreaks of dangerous illnesses and diseases, and can take appropriate action to address the issue.

Figure 6A:
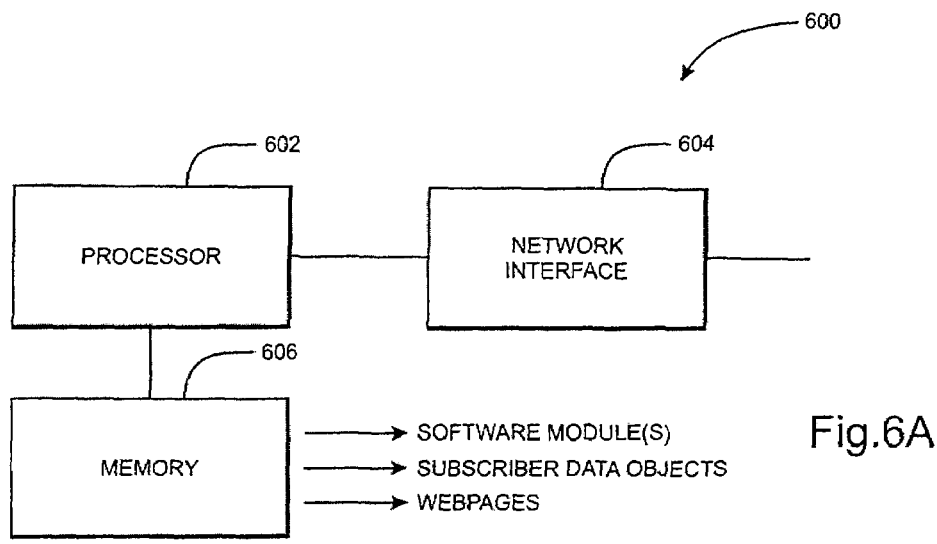
FIG. 6A illustrates a block diagram of an exemplary ICE medical record server in accordance with another embodiment of the invention.

FIG. 6A illustrates a block diagram of an exemplary ICE medical record server 600 in accordance with another embodiment of the invention. The ICE medical record server 600 may be a detailed version of the ICE medical record server 103 of the communication system 100. The ICE medical record server 600 comprises a processor 602, a network interface 604, and a memory 606. The processor 602 performs the various operations of the ICE medical record server 600, five (5) of which are described with reference to FIGS. 6B-6F. The network interface 604 provides an interface to a wide area network for receiving communications therefrom and sending communications thereto. The memory 606, serving generally as a computer readable medium, stores one or more software module(s) for controlling the operations of the processor 602, data objects pertaining to respective subscriber medical records, and possibly other information.

Figure 6B:
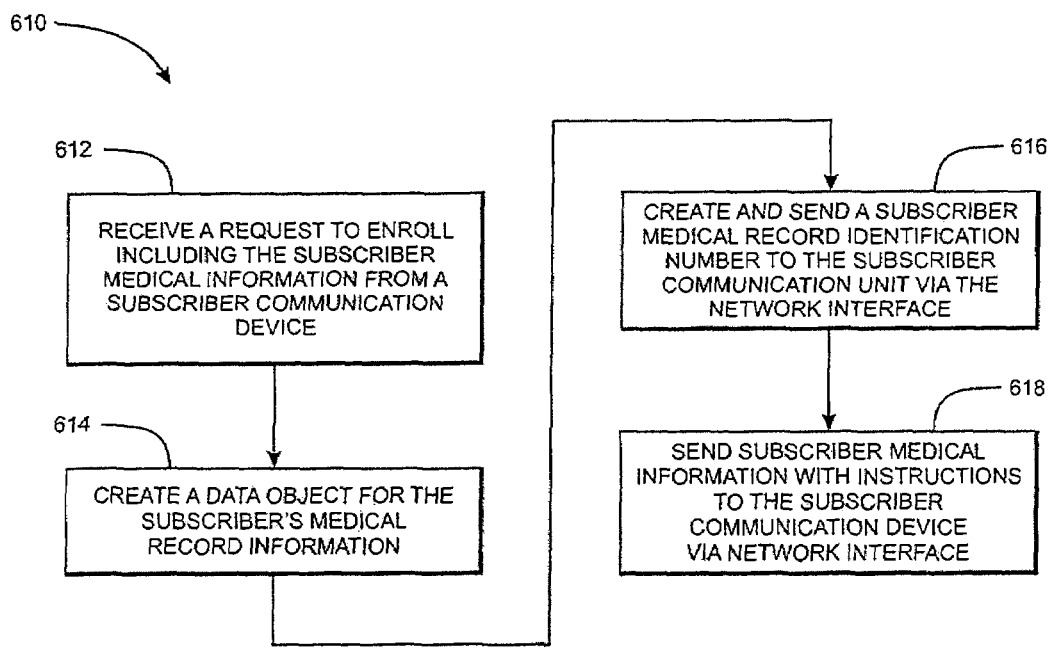
FIG. 6B illustrates a flow diagram of an exemplary method of assisting a candidate subscriber enroll for emergency medical assistance in accordance with another embodiment of the invention.

FIG. 6B illustrates a flow diagram of an exemplary method 610 of assisting a candidate subscriber enroll for emergency medical assistance in accordance with another embodiment of the invention. According to the method 610, the processor 602 receives an enrollment request from a subscriber communication device by way of the network interface 604 (block 612). The enrollment request may contain the subscriber's medical record information, such as those exemplified in FIG. 3. The receiving of the enrollment request may be accomplished in many different ways. For example, upon request the processor 602 may accesses an enrollment webpage from the memory 606, and send the webpage to the requesting subscriber communication device by way of the network interface 604. The enrollment webpage may include an input data object for receiving the requested medical information from the candidate subscriber. The processor 602 then receives the requested subscriber medical information from the subscriber communication device by way of the network interface 604.

After receiving the subscriber's medical record information, the processor 602 creates a data object for the subscriber's medical record information and stores it in the memory 606 (block 614). The data object may have a data structure as exemplified in FIG. 3 discussed above. The processor 602 also generates and sends an ICE identification number associated with the data object to the subscriber communication device by way of the network 604 (block 616).

The processor 602 then sends the subscriber's medical information with instructions to the subscriber communication device by way of the network interface 604 (block 618). This may be accomplished in many different ways. For example, the processor 602 may dynamically create a webpage (e.g., an HTML file) that includes the subscriber's medical information, the identification number, and instructions for the subscriber, and send the webpage to the subscriber communication device by way of the network interface 604. For example, the processor 602 may configure the webpage such that the some or all of the medical information including the ICE identification number is printable in a wallet-size space. The webpage may further contain instructions for the subscriber to print the webpage, cut out the wallet-size space containing the medical information, laminate the cut-out, and place the laminated cut-out into his/her wallet. The webpage may, additionally, provide instructions to the subscriber to enter the ICE identification number along with a website address of a webpage for accessing subscribers' medical records into the subscriber communication device or onto a bracelet or RFID tag to be worn by the subscriber. This could also assist a first responding medical unit to obtain the identification number, and subsequently obtain the subscriber's medical record information using the identification number.

Figure 6C:
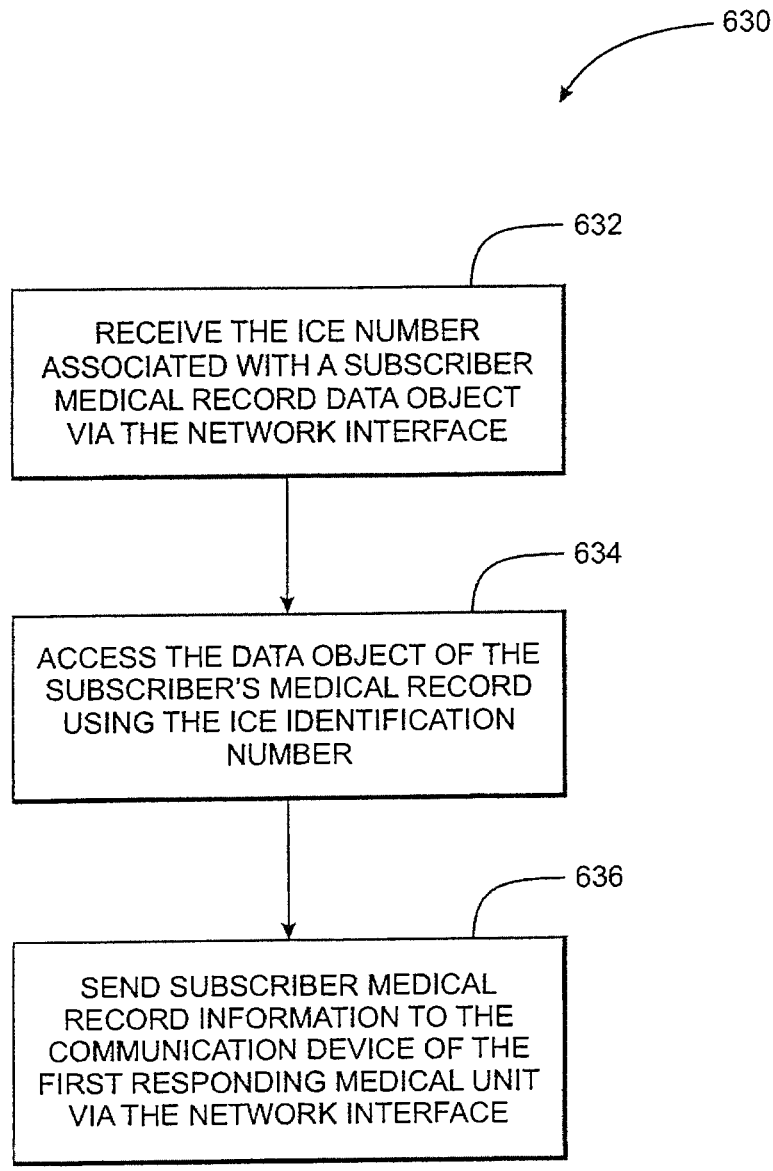
FIG. 6C illustrates a flow diagram of an exemplary method of providing subscriber medical recording information to a first responding medical unit in accordance with another embodiment of the invention.

FIG. 6C illustrates a flow diagram of an exemplary method 630 of providing subscriber medical recording information to a first responding medical unit in accordance with another embodiment of the invention. According to the method 630, the processor 602 receives the ICE identification number associated with a particular subscriber medical record data object by way of the network interface 604 (block 632). This may be accomplished in many different ways. For example, upon request the processor 602 may access a data retrieval webpage (e.g., an HTML file) from the memory 606 and send it to the communication device operated by a first responding medical unit by way of the network interface 604. The data retrieval webpage may include an input data object to receive the ICE identification number associated with the subscriber's medical record data object. In response to the request, the processor 602 sends the data retrieval webpage to the communication device of the first responding medical unit by way of the network interface 604. After sending the data retrieval webpage, the processor 602 may receive the ICE identification number from the communication device of the first responding medical unit by way of the network interface 604.

In response to receiving the ICE identification number, the processor 602 accesses the data object pertaining to the subscriber's medical record from the memory 606 using the ICE identification number (block 634). Then, the processor 602 sends the corresponding subscriber's medical record information to the communication device of the first responding medical unit by way of the network interface 604 (block 636). Having the subscriber's medical information, the first responding medical unit may be able to better diagnose and treat the on-going medical condition of the subscriber. Also, the communication device of the first responding medical unit may be able to pre-populate an electronic patient medical record form with some or all of the information received from the medical record server 600.

Figure 6D:
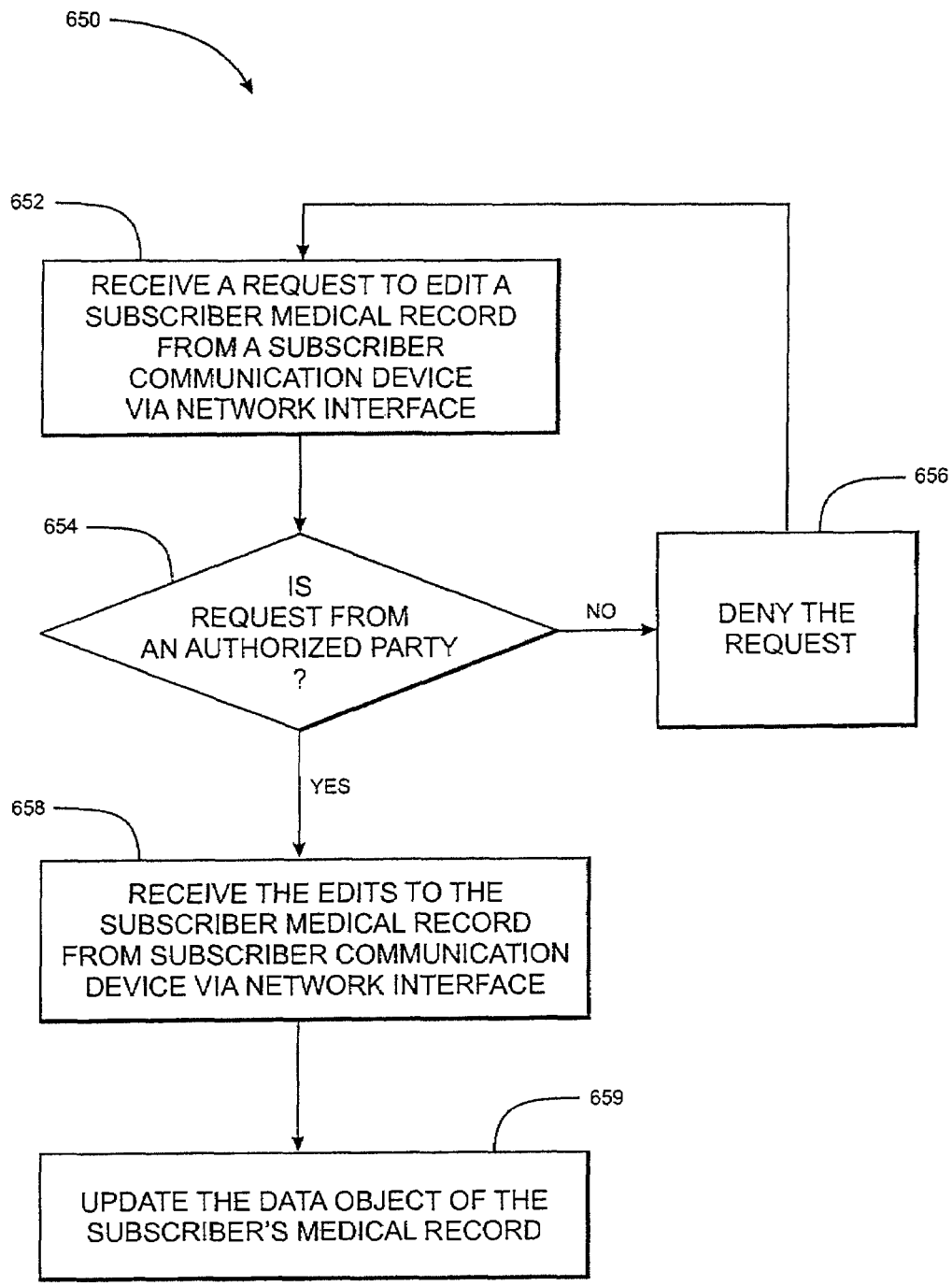
FIG. 6D illustrates a flow diagram of an exemplary method of assisting a subscriber in editing the subscriber medical recording information in accordance with another embodiment of the invention.

FIG. 6D illustrates a flow diagram of an exemplary method 650 of assisting a subscriber in editing the subscriber medical recording information in accordance with another embodiment of the invention. According to the method 650, the processor 602 receives a request to edit the subscriber's medical record information from a subscriber communication device by way of the network interface 606 (block 652). This may be accomplished in many ways. For example, the processor 602 may receive a request for an edit entry webpage (e.g., an HTML file) to allow a subscriber to edit his/her medical record information. The request may be received from a subscriber communication device via the network interface 604. The webpage may include an input data object configured to receive login information (e.g., a username and password) from the subscriber. In response to the request, the processor 602 sends the edit entry webpage to the subscriber communication device by way of the network interface 604. After sending the edit entry webpage, the processor 602 may receive the login information from the subscriber communication device by way of the network interface 604.

After receiving the request to edit the subscriber's medical record, the processor 602 then determines whether the request is from the subscriber (i.e., an authorized party) (block 654). This may be accomplished in many ways. For example, the processor 602 may access a file stored in memory 606 containing username and password combinations. If the processor 602 determines that the login information is not valid, then the processor 602 denies the request (block 656). The processor 602 may deny access by resending the edit entry webpage with an "access denied" message to the subscriber communication unit by way of the network interface 604. This would allow the subscriber to re-submit the username and password in case the subscriber made a typographical error in previously submitting the username and password. Accordingly, the method 650 may return to block 652 where the processor 602 receives another request with possibly valid login information.

If, on the other hand, the processor 602 determines that the login information is valid, the processor 602 receives the edits to the subscriber medical record from the subscriber communication device by way of the network interface 606 (block 658). The processor 602 may accomplish this by sending an edit webpage (e.g., an HTML file) to the subscriber communication device by way of the network interface 604. The edit webpage may include an input data object containing fields pre-populated with the current subscriber's medical information. In this manner, a subscriber is able to change the information in the desired field(s) to make the desired edits to the medical record. After the subscriber makes the edits and submits the information, the processor 602 receives the edited medical record information from the subscriber communication device by way of the network interface 604. The processor 602 then updates the subscriber's medical record data object stored in memory 606 (block 659).

Figure 6E:
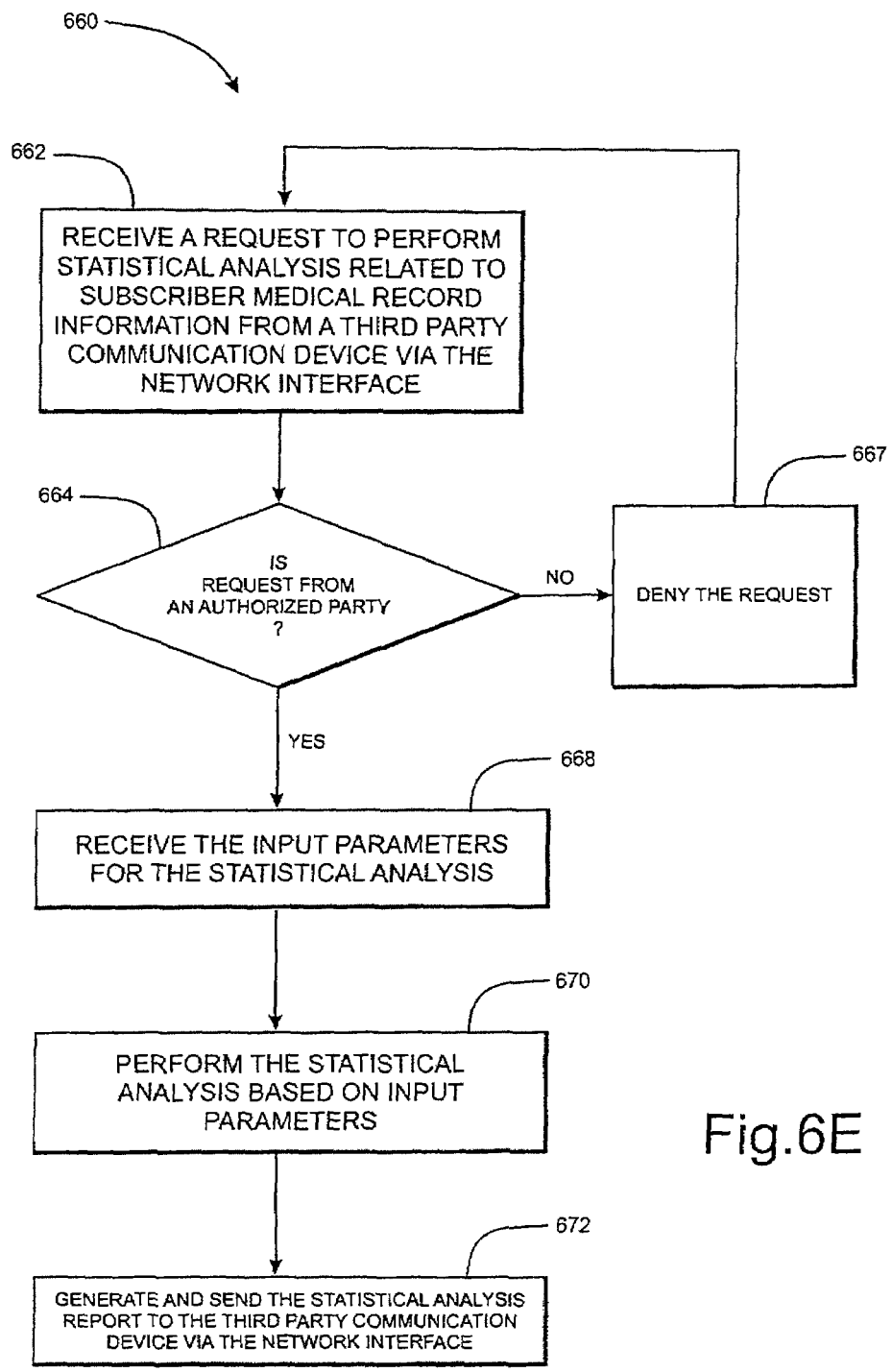
FIG. 6E illustrate a flow diagram of an exemplary method of providing a third party a requested statistical analysis report in accordance with another embodiment of the invention.

FIG. 6E illustrates a flow diagram of an exemplary method 660 of providing a third party a requested statistical analysis report in accordance with another embodiment of the invention. According to the method 660, the processor 602 receives a request to perform statistical analysis related to the subscribers' medical record information from a third party communication device by way of the network interface 604 (block 662). The processor 602 may perform this by initially receiving a request for a report request entry webpage (e.g., an HTML file) from a third party communication device by way of the network interface 604. The report request entry webpage may include an input data object for receiving login information. After receiving the request, the processor 602 accesses the webpage from the memory 606, and sends it to the communication device of the requesting third party by way of the network interface 604. Subsequently, the processor 602 receives the login information from the third party communication device by way of the network interface 604.

Then, the processor 602 determines whether the request to perform statistical analysis comes from an authorized third party (block 664). The processor 602 may perform this task by accessing a file stored in the memory 606 containing valid login information. If the processor 602 determines that the request to perform statistical analysis is not from an authorized party, the processor 602 denies the request (block 667). The method 670 may return back to block 672 to receive another request with possibly valid access information from the third party. If, on the other hand, the processor 602 determines that the request is from an authorized third party, then the processor 602 receives the input parameters for the statistical report from the third party communication device by way of the network interface 604 (block 668). The processor 602 may perform this task by sending a webpage containing an input data object adapted to receive the input parameters for the statistical analysis to the third party communication device by way of the network interface 604. Then subsequently receive the input parameters from the third party communication device by way of the network interface 604.

Once the processor 604 has the input parameters, the processor 602 performs the requested statistical analysis on the subscribers' medical record information stored in the memory 606 based on the input parameters (block 670). After performing the analysis, the processor 602 generates and sends the requested report to the third party communication device by way of the network interface 604 (block 672). In this regard, the processor 602 may dynamically generate a webpage containing the details of the requested report, and send the webpage to the third party communication device by way of the network interface 604.

Figure 6F:
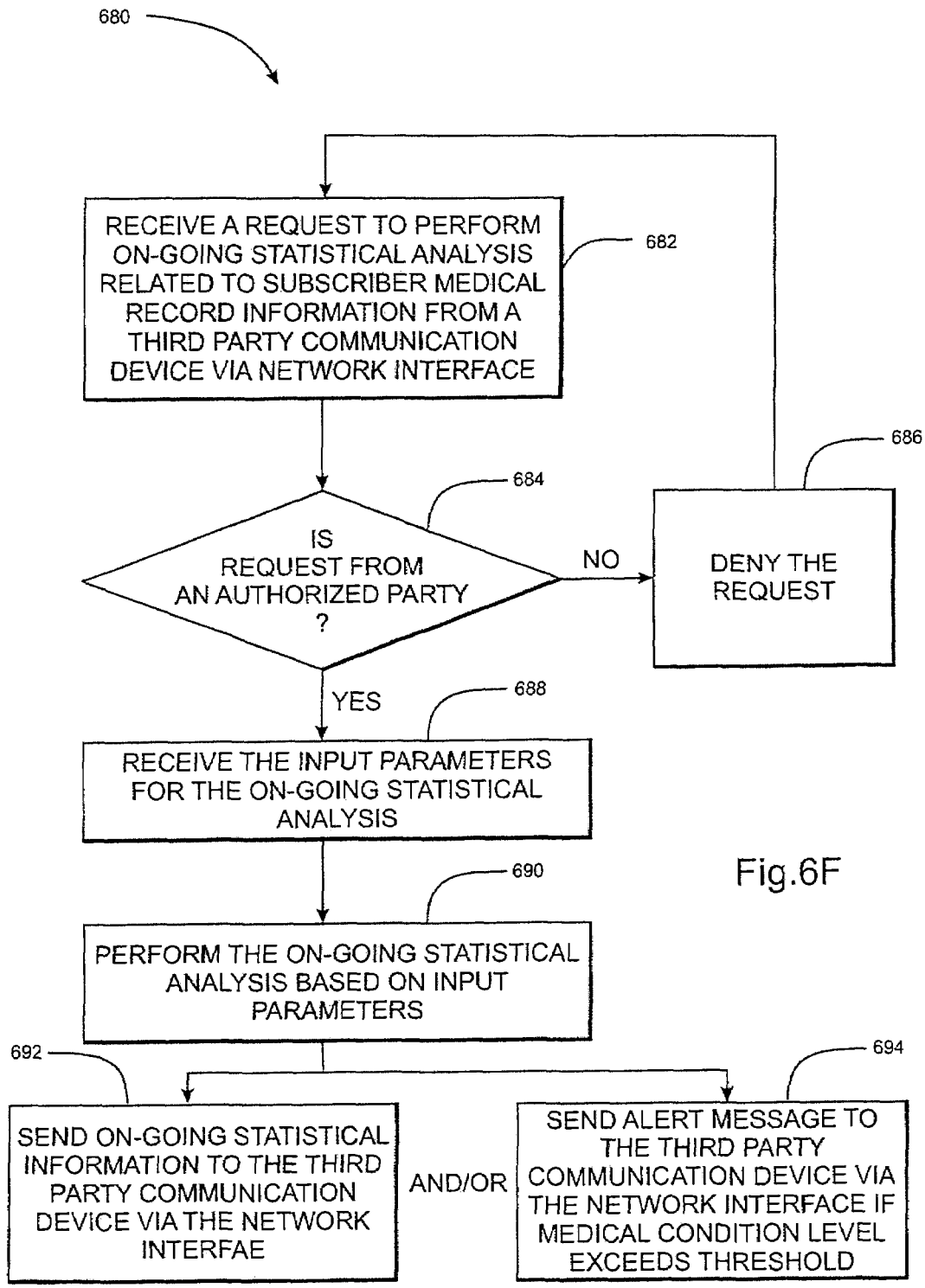
FIG. 6F illustrates a flow diagram of an exemplary method of providing a third party on-going statistical information and/or alerts in accordance with another embodiment of the invention.

FIG. 6F illustrates a flow diagram of an exemplary method 680 of providing a third party on-going statistical information and/or alerts in accordance with another embodiment of the invention. According to the method 680, the processor 602 receives a request to perform on-going statistical analysis related to the subscribers' medical record information from a third party communication device by way of the network interface 604 (block 672). For example, the requested on-going statistical analysis may be to provide statistical information related to the occurrence of one or more specified symptoms, illnesses, and/or diseases. The processor 602 may perform this by initially receiving a request for a medical condition monitoring request entry webpage (e.g., an HTML file) from a third party communication device by way of the network interface 604. The request entry webpage may include an input data object for receiving login information. After receiving the request, the processor 602 accesses the webpage from the memory 606, and sends it to the communication device of the requesting third party by way of the network interface 604. Subsequently, the processor 602 receives the login information from the third party communication device by way of the network interface 604.

Then, the processor 602 determines whether the request came from an authorized third party (block 684). The processor 602 may perform this task by accessing a file stored in the memory 606 containing valid login information. If the processor 602 determines that the request did not come from an authorized party, the processor 602 denies the request (block 686). The method 680 may return back to block 672 to receive another request with valid access information from the third party. If, on the other hand, the processor 602 determines that the request is from an authorized third party, the processor 602 then receives the input parameters for the on-going statistical analysis from the third party communication device by way of the network interface 604 (block 688). The processor 602 may perform this task by sending a webpage containing an input data object adapted to receive the input parameters for the on-going statistical analysis to the third party communication device by way of the network interface 604. Then subsequently receive the input parameters from the third party communication device by way of the network interface 604. The input parameters may be, for example, to monitor for the occurrence of a specific disease within a predefined geographical area, and to provide on-going statistical information related to the occurrences of the disease.

Once the processor 604 has the input parameters, the processor 602 performs the requested on-going statistical analysis based on the input parameters (block 690). While the processor 602 is performing the requested statistical analysis, the processor 602 is sending, on an on-going basis, the corresponding statistical information to the third party communication device by way of the network interface 604 (block 692). Alternatively, or in addition to, the processor 602 may send an alert based on the input parameters to the third party communication device by way of the network interface 604. For example, the input parameters may specify that an alert should be sent when the number of occurrences of the specified disease exceeds a predetermined threshold.

Figure 7A:
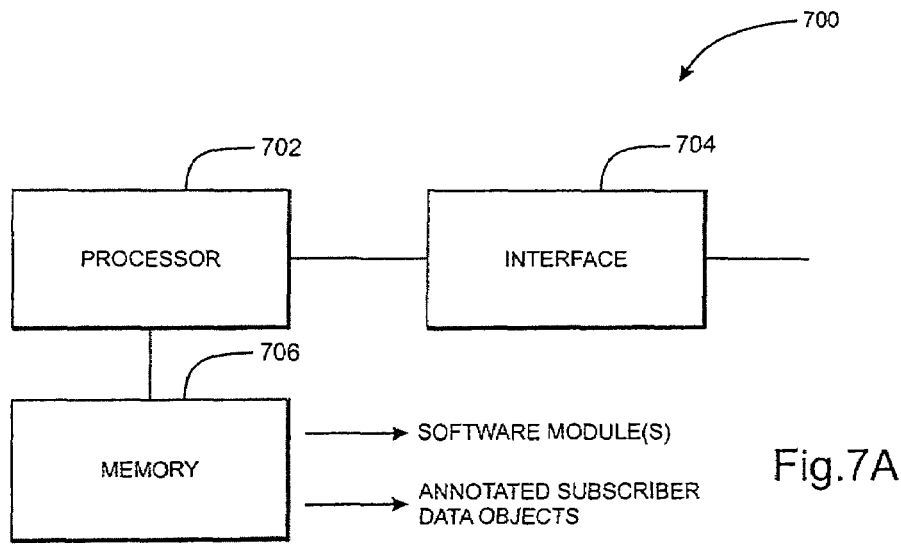
FIG. 7A illustrates a block diagram of an exemplary professional medical record server in accordance with another embodiment of the invention.

FIG. 7A illustrates a block diagram of an exemplary professional medical record server 700 in accordance with another embodiment of the invention. The professional medical record server 700 may be a detailed version of the professional medical record server 104 of the communication system 100. The professional medical record server 700 comprises a processor 702, a network interface 704, and a memory 706. The processor 702 performs the various operations of the professional medical record server 700, three (3) of which are described with reference to FIGS. 7B, 6E, and 6F. The network interface 704 provides an interface to a wide area network for receiving communications therefrom and sending communications thereto. The memory 706, serving generally as a computer readable medium, stores one or more software module(s) for controlling the operations of the processor 702, data objects pertaining to respective subscriber medical records, and possibly other information.

Figure 7B:
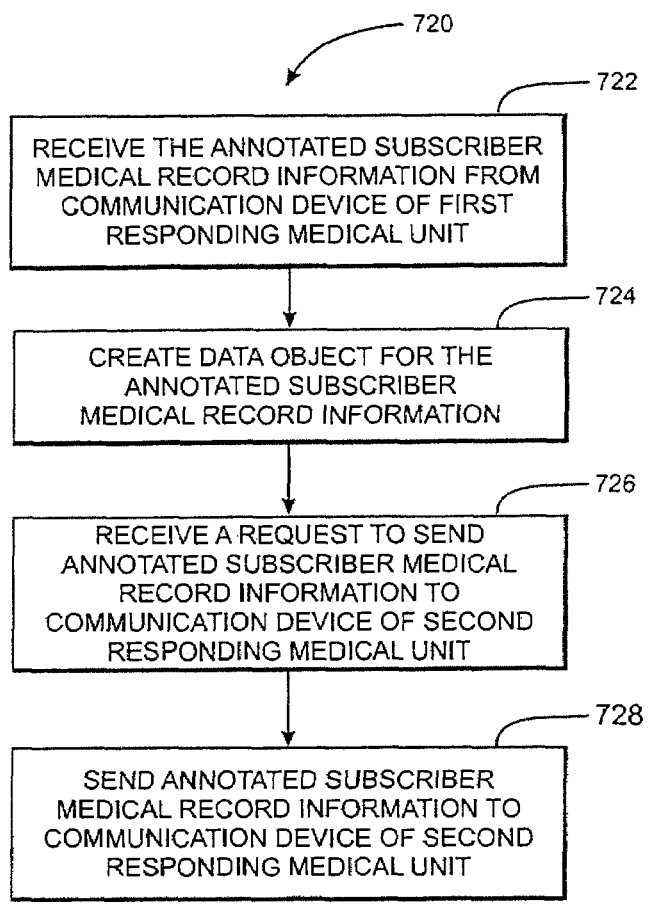
FIG. 7B illustrates a flow diagram of an exemplary method of relaying an annotated subscriber medical record from a first responding medical unit to a second responding medical unit in accordance with another embodiment of the invention.

FIG. 7B illustrates a flow diagram of an exemplary method 720 of relaying an annotated subscriber medical record from a first responding medical unit to a second responding medical unit in accordance with another embodiment of the invention. According to the method 720, the processor 702 receives the annotated subscriber medical record information from the communication device of a first responding medical unit by way of the interface 704 (block 722). This may be the case when the first responding medical unit has annotated the subscriber medical record information with the particulars of the on-going emergency, and has sent the annotated subscriber medical record information to the professional medical record server 700.

After receiving the annotated subscriber medical record information, the processor 702 creates a data object for the annotated subscriber medical record information, and stores the data object into the memory 706 (block 724). Subsequently, the processor 702 may receive a request to forward the annotated subscriber medical record information to the communication device of a second responding medical unit, by way of the interface 704 (block 726). This may be the case where the first responding medical unit is to transport the subscriber to a second responding medical unit (e.g., a hospital, urgent care center, medical clinic, etc.) where the subscriber is to receive further diagnosis and treatment. Then, in response to the request, the processor 702 sends the annotated subscriber medical record information to the communication device of the second responding medical unit by way of the interface 704 (block 728).

As previously discussed, the professional medical record server 700 may perform the same statistical analysis and reporting as provided by the ICE medical record server 600. Accordingly, the professional medical record server 700 may perform the same operations as specified in FIGS. 6E and 6F, illustrating the statistical analysis and reporting operations of the ICE medical record server 600.

Figure 8A:
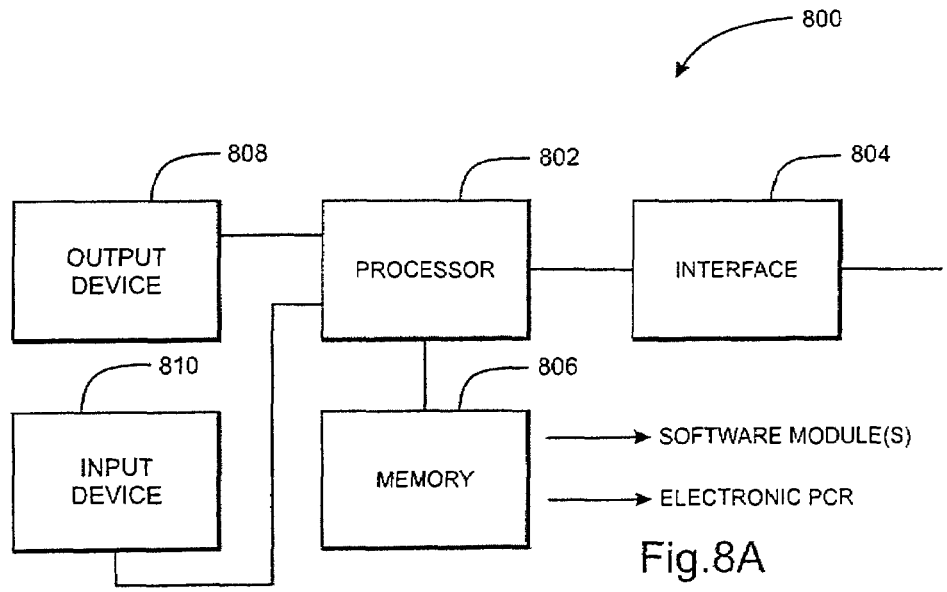
FIG. 8A illustrates a block diagram of an exemplary communication unit of a first responding medical unit in accordance with another embodiment of the invention.

FIG. 8A illustrates a block diagram of an exemplary communication device 800 of a first responding medical unit in accordance with another embodiment of the invention. The communication device 800 comprises a processor 802, an interface 804, an output device 806, an input device 808, and a memory 810. The processor 802 performs the various operations of the communication device 800, two of which are described with reference to FIGS. 8B and 8C. The interface 804 allows the processor 802 to send and receive information to and from the ICE and the professional medical record servers. If the communication device is of a wireless type (e.g., a wireless personal digital assistant (PDA), cellular telephone, or mobile data terminal), the interface 804 could comprise a radio frequency (RF) interface and antenna. If the communication device 800 is not of a wireless type (e.g., a desktop computer), the interface 804 could be a network interface coupled to a wide area network.

The output device 806 may comprise a video display. The input device 808 may comprise a keyboard and/or a pointing device. It shall be understood that the input and output devices 808 and 806 may be integrated, such as in a touch-sensitive display. The memory 810, serving generally as a computer readable medium, stores one or more software module(s) for controlling the operations of the processor 802, and an electronic patient medical record pertaining to the subscriber undergoing medical diagnosis and treatment by the first responding medical unit. The following describes methods implemented by the communication device 800 in obtaining a subscriber's medical record information from a medical record server, and pre-populating an electronic patient medical record form with the information; and a method of annotating and sending the electronic patient medical record to a second responding medical unit.

Figures 8B, 8C:
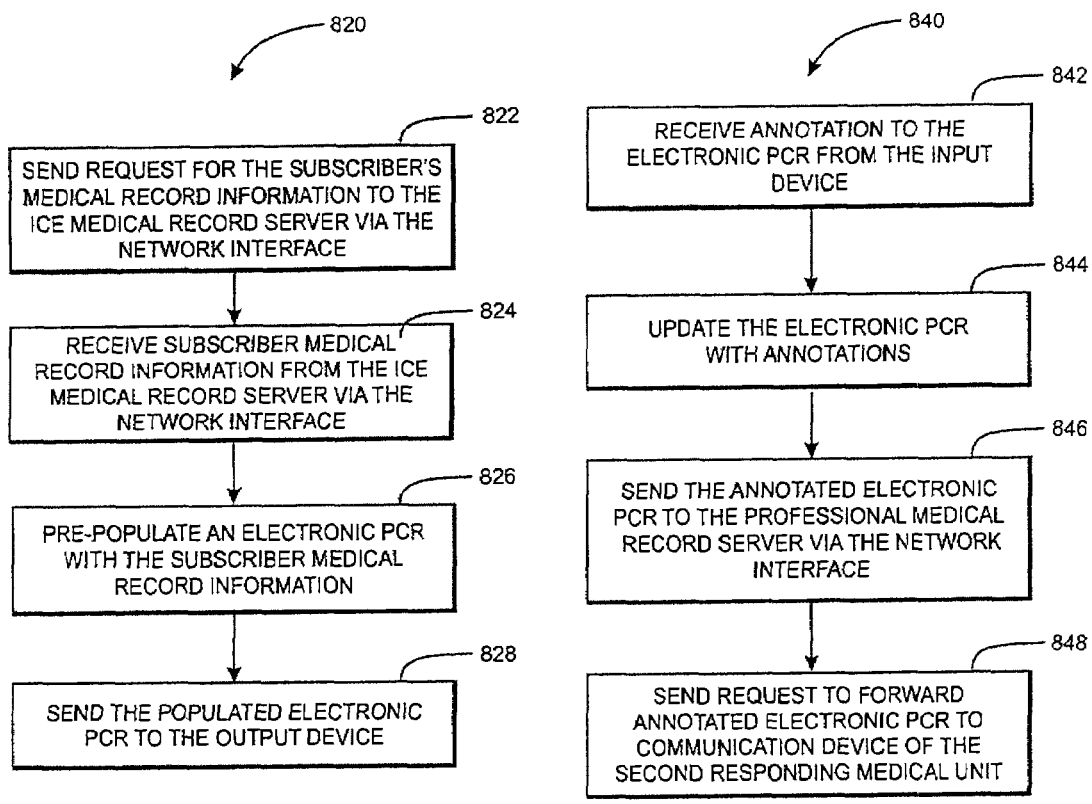
FIG. 8B illustrates a flow diagram of an exemplary method of obtaining subscriber medical record information in accordance with another embodiment of the invention.
FIG. 8C illustrates a flow diagram of an exemplary method of providing the subscriber medical information to a second responding medical unit in accordance with another embodiment of the invention.

FIG. 8B illustrates a flow diagram of an exemplary method 820 of obtaining subscriber medical record information in accordance with another embodiment of the invention. According to the method 820, the processor 802 sends a request for the medical record information pertaining to a subscriber to the ICE medical record server by way of the interface 804 (block 822). The processor 802 may perform this by sending the ICE identification number corresponding to the subscriber's medical record to the ICE medical record server. In more detail, the processor 802 may send a request for a data retrieval webpage to the medical record server by way of the interface 804. The processor 802 may perform this operation in response to a user entering the webpage address via the input device 808. The processor 802 then receives the data retrieval webpage (e.g., HTML file) by way of the interface 804. The data retrieval webpage may include an input data object for receiving the ICE identification number from a first responding medical unit. The processor 802 then receives the ICE identification number from the input device 808. This may be the case where the first responding medical unit obtains the ICE identification number from the subscriber, and enters the number into the communication device 800. The processor 802 then sends the ICE identification number to the ICE medical record server by way of the interface 804.

Subsequently, the processor 802 receives the medical record information from the ICE medical record server by way of the interface 804 (block 824). The processor 802 may then pre-populate an electronic patient medical record form (e.g., a PCR form) with some or all of the medical record information it has received from the ICE medical record server (block 826). The processor 802 also sends the electronic patient medical record information to the output device 806 for viewing by the first responding medical unit (block 828).

FIG. 8C illustrates a flow diagram of an exemplary method 840 of providing annotated subscriber medical information to a second responding medical unit in accordance with another embodiment of the invention. Once the electronic patient medical record form has been populated with the subscriber's medical record information according to the method 820 previously described, the processor 802 receives annotations to the electronic patient medical record from the input device 810 (block 842). This may be the case where the first responding medical unit has entered information into the communication device 800 concerning the on-going emergency. Such annotations may include, as exemplified in FIG. 4C, information related to the patient's complaint, dispatch information, physical assessment, procedure administered, patient assessment, and any other information that may assist a second responding medical unit with the diagnosis and treatment of the subscriber.

The processor updates the electronic patient medical record with the annotations and saves it into the memory 806 (block 844). In response to receiving an instruction from the input device 810, the processor 702 sends the annotated electronic patient medical record to the professional medical record server by way of the interface 804 (block 846). Then, in response to receiving another instruction from the input device 810, the processor 802 sends a request to the professional medical record server to forward the annotated subscriber medical record information to the communication device of a second responding medical unit. The request would include information as to the electronic address of the communication device of the second responding medical unit.

Thus, using the subscriber medical record information it has received from the medical record server, the first responding medical unit may be able to better diagnose and treat the subscriber. Also, because the communication device 800 is capable of pre-populating an electronic patient medical record form with the subscribers medical record information, it saves the first responding medical unit a substantial amount of time from entering the information manually. And, in fact, if the subscriber is unconscious, without the communication device 800 the first responding medical unit may not be able to complete the electronic patient medical record form for the subscriber. Further, the communication device 800 allows the first responding medical unit to annotate the electronic patient medical record to document the on-going emergency. Finally, the communication device 800 allows the first responding medical unit to send the annotated electronic patient medical record, via the professional medical record server, to a second responding medical unit to which the subscriber will be taken after receiving preliminary diagnosis and treatment from the first responding medical unit.

Figure 9A:
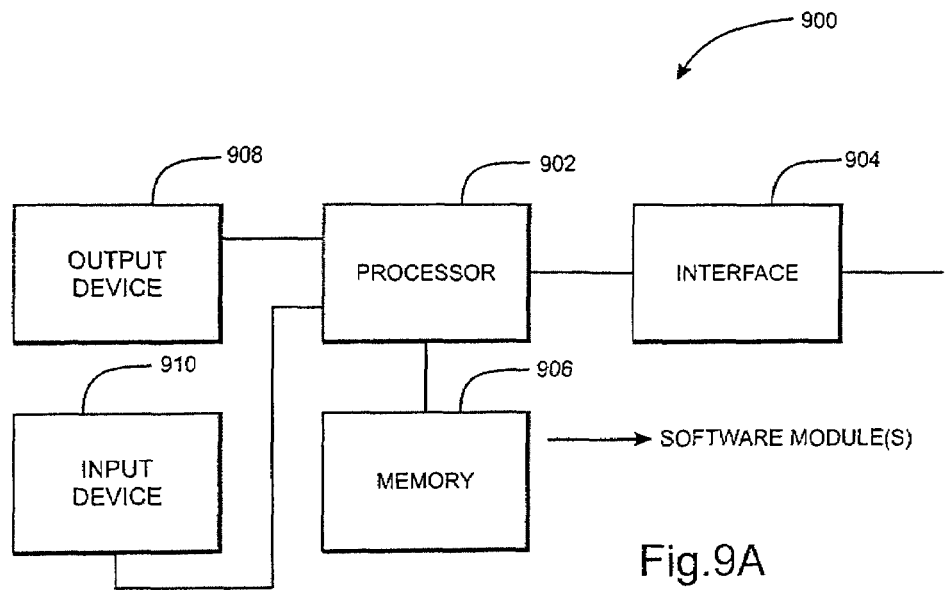
FIG. 9A illustrates a block diagram of an exemplary communication device of a third party in accordance with another embodiment of the invention.

FIG. 9A illustrates a block diagram of an exemplary communication device 900 of a first responding medical unit in accordance with another embodiment of the invention. The communication device 900 comprises a processor 902, an interface 904, an output device 906, an input device 908, and a memory 910. The processor 902 performs the various operations of the communication device 900, two of which are described with reference to FIGS. 9B and 9C. The interface 904 allows the processor 902 to send and receive information to and from the ICE and the professional medical record servers. If the communication device is of a wireless type (e.g., a wireless personal digital assistant (PDA), cellular telephone, or mobile data terminal), the interface 904 could comprise a radio frequency (RF) interface and antenna. If the communication device 900 is not of a wireless type (e.g., a desktop computer), the interface 904 could be a network interface coupled to a wide area network.

Figures 9B, 9C:
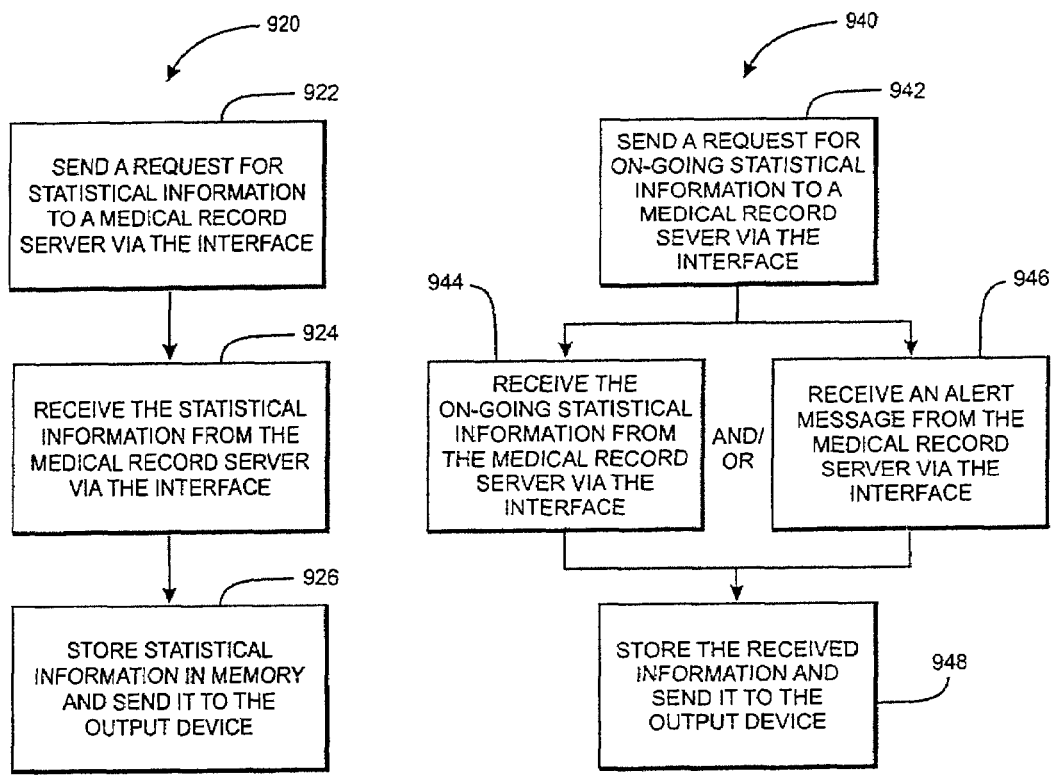
FIG. 9B illustrates a flow diagram of an exemplary method of requesting and receiving statistical information from a medical record server in accordance with another embodiment of the invention.
FIG. 9C illustrates a flow diagram of an exemplary method of requesting and receiving on-going statistical information and/or alerts from a medical record server in accordance with another embodiment of the invention.

FIG. 9B illustrates a flow diagram of an exemplary method 920 of requesting and receiving statistical information from a medical record server in accordance with another embodiment of the invention. As previously discussed, the ICE and professional medical record servers hold valuable medical information related to many subscribers. Thus, a third party, such as a government agency or medical institution, may desire to obtain statistical information related to the subscribers' medical information. Also as discussed, such third party may desire such statistical information to perform symptomatic surveillance in order to monitor for the outbreak of specified illnesses and diseases. In addition, in case of a wide area disaster, a third party, such as a government agency like FEMA, may desire statistical information related to subscribers' recently treated by first responding medical units in response to the disaster. In this way, the government agency can more efficiently and effectively allocate resources to address the wide area disaster.

According to the method 920, the processor 902, in response to receiving instructions from the input device 910, sends a request for statistical information to any of the medical record server by way of the interface 904 (block 922). The request may further contain the input parameters for the requested statistical report. For example, the input parameters may specify delimiters such as female subscribers between the ages of 35 and 55 living in a particular geographical area, and outputs such as the number of occurrences of such female subscribers with breast cancer and the corresponding percentage of the female subscribers. As another example, the input parameters may specify delimiters such as subscribers' seen by first responding medical units within the last three hours, and an output specifying a breakdown of the primary complaint of the subscribers. After sending the request, the processor 902 receives the requested statistical information by way of the interface 904 (block 924). The processor 902 then stores the information into the memory 926, and may send the information to the output device 908 for viewing by the third party (block 926).

FIG. 9C illustrates a flow diagram of an exemplary method 940 of requesting and receiving on-going statistical information from a medical record server in accordance with another embodiment of the invention. As previously discussed, the medical information held by any of the medical record servers may be used to monitor, on an on-going basis, for certain abnormalities related to the occurrence of specified symptoms, illnesses, and/or diseases. For example, a government agency or medical institution may want to monitor for the outbreaks of potentially life-threatening diseases, such as severe acute respiratory syndrome (SARS), within a specified geographical area. As discussed below, a third party may receive on-going statistical information related to such specified medical conditions, as well as alerts when the number of occurrences of the specified medical conditions exceed a predetermined threshold.

According to the method 940, the processor 902, in response to receiving instructions from the input device 910, sends a request for on-going statistical information to any of the medical record server by way of the interface 904 (block 942). The request may further contain the input parameters for the on-going statistical analysis and information. For example, the input parameters may specify delimiters such as subscribers living in California, and outputs such as the number of occurrences of subscribers contracting SARS up-to-date within the calendar year and an alert request when the number exceeds eight (8). After sending the request, the processor 902 receives, on an on-going basis, the requested statistical information, and possibly an alert message by way of the interface 904 (block 944 and/or 946). For example, the received information may indicate that nine (9) subscribers to-date within the current calendar year have contracted SARS. The received information may further include an alert message since the number of occurrences of SPARS has exceeded the specified threshold of eight (8). The processor 902 then stores the information into the memory 926, and sends the information into the output device 908 for viewing by the third party (block 948).

While the invention has been described in connection with various embodiments, it will be understood that the invention is capable of further modifications. This application is intended to cover any variations, uses or adaptation of the invention following, in general, the principles of the invention, and including such departures from the present disclosure as come within the known and customary practice within the art to which the invention pertains.

What is claimed is:

1. A communication system, comprising:
   a network;
   a first communication device operated by a first medical unit by way of said network;
   a first medical record server adapted to:
      receive an identification number associated with a data object pertaining to a medical record of a subscriber from the first communication device; and in response to receiving said identification number, send medical information from said data object to said first communication device by way of said network, wherein said first communication device is further adapted to receive said medical information from said first medical record server by way of said network, receive an annotation to said medical information from said first medical unit, and modify said medical information to include said annotation; and a second medical record server, wherein said first communication device is adapted to send said annotated medical information to said second medical record server, and said second medical record server is further adapted to:

receive a request for statistical information related to medical information pertaining to a plurality of medical records pertaining to respective subscribers from a second communication device by way of said network, wherein each of said medical records includes an annotation from a medical unit responding to a medical emergency associated with a corresponding subscriber, and wherein said request includes input parameters related to said statistical information;

perform an analysis on a basis of said input parameters to generate said statistical information; and send said statistical information to said second communication device by way of said network.

2. The communication system of claim 1, wherein said data object comprises any two or more of the following:
demographic information related to said subscriber;
in-case-of-emergency contact information related to said subscriber;
medical insurance information related to said subscriber;
primary care information related to said subscriber;
health information related to said subscriber.

3. The communication system of claim 1, further comprising said first communication device, and wherein said first communication device is adapted to:
receive said medical information from said data object; and
pre-populate an electronic subscriber medical record form with said medical information.

4. The communication system of claim 3, wherein said electronic subscriber medical record form comprises a pre-hospital care record (peR) form.

5. The communication system of claim 1, wherein said medical record server and said second medical record server operate on a common server.

6. The communication system of claim 1, further comprising a second communication device, and wherein said second medical record server is adapted to send said annotated medical information to said second communication device.

7. The communication system of claim 6, wherein said second communication device is operated by a second medical unit.

8. The communication system of claim 1, wherein said second medical record server is further adapted to:
receive a request to perform on-going statistical analysis related to medical information pertaining to a plurality of medical records of respective subscribers from a second communication device by way of said network, wherein each of said medical records includes an annotation from a medical unit responding to a medical emergency associated with a corresponding subscriber, and wherein said request includes input parameters related to said on-going statistical analysis; and perform said on-going analysis to generate said on-going statistical information.

9. The communication system of claim 8, wherein said second medical record server is adapted to send said on-going statistical information to said second communication device by way of said network.

10. The communication system of claim 8, wherein said medical record server is adapted to send an alert on a basis of said input parameters to said second communication device by way of said network.

11. The communication system of claim 1, wherein said annotation includes information related to an on-going medical emergency concerning said subscriber.

12. The communication system of claim 1, wherein said medical record server is further adapted to:
receive an enrollment request from a second communication device operated by a user by way of said network, wherein said enrollment request includes medical information related to said user;
create a second data object comprising said medical information of said user;
generate a second identification number associated with said second data object; and
send said second identification number to said second communication device by way of said network.

13. The communication system of claim 12, wherein said medical record server is further adapted to:
generate a webpage containing said medical information of said user and said second identification number; and
send said webpage to said second communication device by way of said network.

14. The communication system of claim 13, wherein said webpage includes instructions to have said second identification number stored in any one of a radio frequency identification (RFID) tag, a bracelet, or in said second communication device.

15. The communication system of claim 1, wherein said medical record server is further adapted to:
receive a request to edit said medical information in said data object from a second communication device operated by said subscriber;
determine whether said request is valid; and
if said request is invalid, send a message denying said request to said second communication device by way of said network; or
if said request is valid,
receive edits to said medical information in said data object from said second communication device by way of said network; and
update said data object to reflect said edits.

16. The communication system of claim 1, wherein said medical record server is further adapted to:
receive a request for statistical information related to medical information pertaining to a plurality of medical records of respective subscribers from a second communication device by way of said network, wherein said request includes input parameters related to said statistical information;
perform an analysis on a basis of said input parameters to generate said statistical information;
send said statistical information to said second communication device by way of said network.

17. The communication system of claim 1, wherein said medical record server is further adapted to:
receive a request to perform on-going statistical analysis related to medical information pertaining to a plurality of medical records of respective subscribers from a second communication device by way of said network, wherein said request includes input parameters related to said on-going statistical analysis; and perform said on-going analysis on a basis of said input parameters to generate on-going statistical information.

18. The communication system of claim 17, wherein said medical record server IS adapted to send said on-going statistical information to said second communication device by way of said network.

19. The communication system of claim 17, wherein said medical record server is adapted to send an alert on a basis of said input parameters and said statistical information to said second communication device by way of said network.

20. A medical record server, comprising:
an interface;
a memory; and
a processor adapted to:
receive an identification number associated with a data object pertaining to a medical record of a subscriber from a first communication device operated by a medical unit by way of said interface;
access said data object from said memory;
send medical information from said data object to said first communication device by way of said interface;
receive a request for statistical information related to medical information pertaining to a plurality of medical records of respective subscribers from a second communication device by way of said interface, wherein said request includes input parameters related to said statistical information;
perform an analysis on a basis of said input parameters to generate said statistical information; and
send said statistical information to said second communication device by way of said interface.

21. The medical record server of claim 20, wherein said data object comprises any two or more of the following:
demographic information related to said subscriber;
in-case-of-emergency contact information related to said subscriber;
medical insurance information related to said subscriber;
primary care information related to said subscriber;
health information related to said subscriber.

22. The medical record server of claim 20, wherein said processor IS further adapted to:
receive an enrollment request from a second communication device operated by a user by way of said interface, wherein said request includes medical information related to said user;
create a second data object comprising said medical information of said user;
generate a second identification number associated with said second data object; and
send said second identification number to said second communication device by way of said interface.

23. The medical record server of claim 20, wherein said processor is further adapted to:
receive a request to edit said medical information in said data object from a second communication device operated by said subscriber by way of said interface;
determine whether said request is valid; and
if said request is invalid, send a message denying said request to said second communication device by way of said interface; or
if said request is valid,
receive edits to said medical information in said data object from said second communication device by way of said interface; and
update said data object to reflect said edits.

24. The medical record server of claim 20, wherein said processor IS further adapted to:
receive a request to perform on-going statistical analysis related to medical information pertaining to a plurality of medical records of respective subscribers from a second communication device by way of said interface, wherein said request includes input parameters related to said on-going statistical analysis; and
perform said on-going analysis on a basis of said input parameters to generate on-going statistical information.

25. The medical record server of claim 24, wherein said processor is adapted to send said on-going statistical information to said second communication device by way of said interface.

26. The medical record server of claim 24, wherein said processor is adapted to send an alert on a basis of said input parameters and said on-going statistical information to said second communication device by way of said interface.

27. A medical record server, comprising:
an interface;
a memory storing a plurality of data objects containing medical information pertaining to respective subscribers, wherein said medical information includes annotations from medical units responding to medical emergencies associated with said respective subscribers; and
a processor adapted to:
receive a request for statistical information related to said medical information pertaining to said respective subscribers, wherein said request includes input parameters related to said statistical information, and wherein said request is received from a communication device by way of said interface;
perform an analysis on a basis of said input parameters to generate said statistical information;
send said statistical information to said communication device by way of said interface.

28. A medical record server, comprising:
an interface;
a memory storing a plurality of data objects containing medical information pertaining to respective subscribers, wherein said medical information includes annotations from medical units responding to medical emergencies associated with said respective subscribers; and
a processor adapted to:
receive a request to perform on-going statistical analysis related to said medical information pertaining to said respective subscribers, wherein said request includes input parameters for said on-going statistical analysis, and wherein said request is received from a communication device by way of said interface; and
perform said on-going analysis to generate on-going statistical information.

29. The medical record server of claim 28, wherein said processor is adapted to send said on-going statistical information to said communication device by way of said interface.

30. The medical record server of claim 28, wherein said processor is adapted to send an alert on a basis of said input parameters and said on-going statistical information to said communication device by way of said interface.

31. A communication device, comprising:
an interface; and
a processor adapted to:
send a request for statistical information related to medical information pertaining to respective subscribers to a medical record server by way of said interface, wherein said medical information includes annotations from medical units responding to medical emergencies associated with said respective subscribers, and wherein said request includes input parameters related to said statistical information; and receive said statistical information by way of said interface.

32. A communication device, comprising:

an interface; and a processor adapted to:

send a request for on-going statistical information related to medical information pertaining to respective subscribers to a medical record server by way of said interface, wherein said medical information includes annotations from medical units responding to medical emergencies associated with said respective subscribers, and wherein said request includes input parameters related to said ongoing statistical information; and receive said on-going statistical information from said medical record server by way of said interface; or receive an alert on a basis of said input parameters and said on-going statistical information from said medical record server by way of said interface.

* * * * *